US008871167B2

(12) United States Patent
Aizawa et al.

(10) Patent No.: US 8,871,167 B2
(45) Date of Patent: Oct. 28, 2014

(54) BIOCOMPATIBLE CERAMIC-POLYMER HYBRIDS AND CALCIUM PHOSPHATE POROUS BODY

(75) Inventors: Mamoru Aizawa, Kawasaki (JP); Masahiro Rikukawa, Yokohama (JP); Yusuke Shigemitsu, Tokyo (JP); Hiroshi Nagashima, Kawasaki (JP)

(73) Assignees: Meiji University, Tokyo (JP); Showa Ika Kogyo Co. Ltd., Aichi-ken (JP)

( * ) Notice: Subject to any disclaimer, the term of this patent is extended or adjusted under 35 U.S.C. 154(b) by 163 days.

(21) Appl. No.: 13/308,459

(22) Filed: Nov. 30, 2011

(65) Prior Publication Data

US 2012/0136088 A1    May 31, 2012

Related U.S. Application Data

(63) Continuation-in-part of application No. 12/621,274, filed on Nov. 18, 2009.

(60) Provisional application No. 61/138,016, filed on Dec. 16, 2008.

(30) Foreign Application Priority Data

Mar. 22, 2011   (JP) .................................. 2011-062997

(51) Int. Cl.
| C01B 15/16 | (2006.01) |
| C01B 25/26 | (2006.01) |
| A61L 27/56 | (2006.01) |
| A61L 27/42 | (2006.01) |

(52) U.S. Cl.
CPC ............... *A61L 27/425* (2013.01); *A61L 27/56* (2013.01)
USPC .......................................... 423/311; 423/308

(58) Field of Classification Search
CPC ............................. A61L 27/425; A61L 27/56
USPC .......................................................... 523/115
See application file for complete search history.

(56) References Cited

FOREIGN PATENT DOCUMENTS

| JP | 2003093052 A | * | 4/2003 | ............... C12N 5/06 |
| JP | 2004284933 A | * | 10/2004 | ............... C01B 25/32 |
| JP | 2008-156213 A |  | 7/2008 |  |

OTHER PUBLICATIONS

Aizawa et al., Machine generated English translation of JP 2004-284933 A, Oct. 4, 2004.*
JP 2003-093052 A Machine-generated English translation, Aizawa, M., Apr. 2, 2003.*
Preprints for The Society of Polymer Science, Japan, vol. 56, No. 2, (2007), p. 2U14 (4 pages).
Preprints for The Society of Polymer Science, Japan, vol. 56, No. 2, (2007), p. 2U16 (4 pages).
Preprints for The Society of Polymer Science, Japan, vol. 56, No. 2, (2007), p. 3Z05 (4 pages).

(Continued)

*Primary Examiner* — Mark Eashoo
*Assistant Examiner* — David Karst
(74) *Attorney, Agent, or Firm* — Osha Liang LLP

(57) ABSTRACT

A hydroxyapatite ceramic hybrid material, which includes a biodegradable polymer included in the pores in a hydroxyapatite ceramic structure, and a method thereof, and a calcium phosphate porous body, which is formed by an intertwining of fibrous calcium phosphates and includes a plurality of first pores formed where the fibrous calcium phosphates interconnect and plurality of equal diameter substantially spherical second pores with a larger inside diameter than the first pores, and a method thereof are provided.

13 Claims, 30 Drawing Sheets

(56) References Cited

OTHER PUBLICATIONS

Notice of Reasons for Rejection (Official Action) mailed Dec. 17, 2013, by the Japan Patent Office in corresponding Japanese Patent Application No. 2009-284999, with English translation (10 pages).
Fall Meeting of the Ceramic Society of Japan, vol. 20th, [2G21], 2007; p. 147 (3 pages).
Preprints for The Society of Polymer Science, Japan, vol. 56, No. 1, (2007), p. 2Pf178 (3 pages).
Preprints for The Society of Polymer Science, Japan, vol. 56, No. 1, (2007), p. 2Pe179 (3 pages.
Journal of Japanese Society for Biomaterials, vol. 23, No. 5, (2005), pp. 336-342 (9 pages).

* cited by examiner

FIG. 2

```
┌─────────────────────────────┐
│   Prepare a Slurry of       │──── 21
│ Hydroxyapatite Fibers and   │
│       Carbon Beads          │
└─────────────────────────────┘
              │
              ▼
┌─────────────────────────────┐
│     Add Agar to Slurry      │──── 22
└─────────────────────────────┘
              │
              ▼
┌─────────────────────────────┐
│     Make a Green Compact    │──── 23
└─────────────────────────────┘
              │
              ▼
┌─────────────────────────────┐
│   Fire the Green Compact to │──── 24
│     Produce Porous Ceramic  │
└─────────────────────────────┘
              │
              ▼
┌─────────────────────────────┐
│       Make HAp-PLLA         │──── 25
│      Hybrid Materials       │
└─────────────────────────────┘
```

FIG. 3

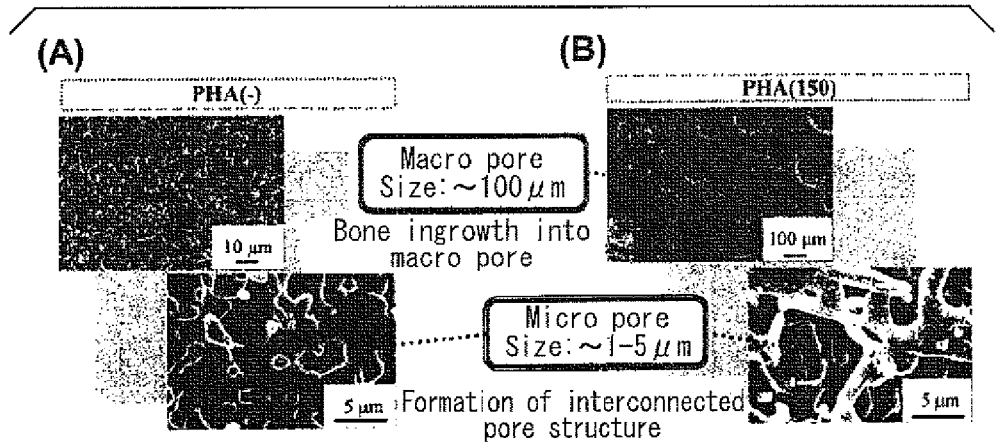

Microstructure of cross section of typical HAp/PLLA hybrids

BIOCOMPATIBLE CERAMIC-POLYMER HYBRIDS AND CALCIUM PHOSPHATE POROUS BODY

Priority is claimed on U.S. patent application Ser. No. 12/621,274, filed Nov. 18, 2009, the content of which is incorporated herein by reference.

FIELD OF THE INVENTION

The present invention relates to composite materials for bone repair or replacement, more particularly to composite materials comprising hydroxyapatite (HAp) and a biocompatible polymer. Also, the present invention relates to a calcium phosphate porous body and a method for manufacturing the same.

BACKGROUND OF INVENTION

Many medical conditions, such as bone fracture, involve damages to the hard tissues (e.g., bones). Such conditions need materials that can be used to repair the hard tissue damages. With increasing life expectancy, the need for such materials is expected to increase substantially.

The materials used in such repairs often need to have sufficient mechanical strength to substitute for the functions of the damage hard tissues. These materials may be used temporarily, i.e., until the hard tissue repairs itself, or they may be used as permanent replacements. Various materials used in such hard tissue repairs include ceramic materials.

Currently, there are three types of ceramics that are clinically used for such purposes. Bioactive ceramics are materials that can directly bond with host bone. Examples of such materials include hydroxyapatite ($Ca_{10}(PO_4)_6(OH)_2$: HAp). The second type of bioceramics is biodegradable ceramics (bioabsorbable ceramics). These materials can be gradually resorbed in the body. Such biodegradable materials include, for example, β-tricalcium phosphates ($\beta$-$Ca_3(PO_4)_2$: β-TCP). The third type of bioceramics is bio-inert ceramics. These materials are stable in the living body and have high mechanical strength. Examples of bio-inert ceramic materials include α-alumina ($\alpha$-$Al_2O_3$) and tetragonal zirconium (t-$ZrO_2$).

As a specific example of a bioabsorbable ceramic, Japanese Unexamined Patent Application, Publication No. 2004-284933 discloses fibrous calcium phosphate composed of tricalcium phosphate. Japanese Unexamined Patent Application, Publication No. 2004-284933 notes that a porous calcium phosphate compact formed using fibrous calcium phosphate comprises pores that absorb cells, and pores that absorb the culture medium required for cellular growth. This is conducive to the growth of bone tissue or similar inside the compact.

HAp is a natural composition found in teeth and bones within the human body. Thus, HAp has an excellent biocompatibility and, therefore, would be a good candidate material for hard tissue replacements or repairs. Indeed, it is commonly used as a filler to replace damaged bone or as a coating to promote bone in-growth on prosthetic implants. Some medical implants, e.g. hip replacements or dental implants, are coated with hydroxyapatite, and it has been found that HAp may promote osseo-integration of these artificial implants.

Because of these favorable properties of HAp, there has been an immense interest in further developing and improving this material for medical use. Various methods have been disclosed for modifying HAp and other implant materials to improve their bone adhesion and other properties. For example, it has been shown that coating this material with bone morphogenetic proteins can improve cell adhesion and subsequent tissue attachment. See, Zeng, H., et al., Biomaterials 20 (1999): 377-384. Another commonly used modification is nitridation, which improves the hardness of HAp and its chemical inertia to the biological environment. See, Habelitz, S., et al., J. European Ceramic Society 19 (1999): 2685-2694, and Torrisi, L., Metallurgical Science and Technology 17(1) (1999): 27-32.

More recently, U.S. Pat. No. 7,211,271 issued to Risbud et al., combines these two approaches (i.e., nitridation and coating with a bone morphogenetic protein or an analog thereof, or DNA encoding such a protein or analog) to produce HAp that facilitates the growth of tissues on such materials.

Although HAp and modified HAp materials have excellent biocompatibilities and beneficial tissue/bone formation stimulating effects, the mechanical strengths, especially the toughness value and Young's modulus, of hydroxyapatite materials are substantially different from those of living cortical bones. As a result, the use of HAp in bone repair or replacement may lead to undesired stress around the junctions of these artificial materials and the natural bones. Such undesired stress will eventually lead to junction failures. Thus, there remains a need for new materials that would have the benefits of HAp, but with mechanical properties more similar to those of natural bones.

A bioabsorbable ceramic used in the repair of hard tissue damage also needs to have sufficient strength to maintain the function of the damaged hard tissue, while allowing for the rapid infusion of cells to be replaced with autologous bone growth or the like.

However, in a porous body composed of conventionally tricalcium phosphate, it is difficult to interconnect a plurality of pores for the suitable infusion of cells, while maintaining practical strength and the speed of bone growth is insufficient.

SUMMARY OF INVENTION

One aspect of the invention relate to HAp ceramic hybrid materials. A HAp ceramic hybrid material in accordance with one embodiment of the invention includes a HAp ceramic structure having pores therein; and a biodegradable polymer included in the pores in the HAp ceramic structure. The pores may account for 40-70% volume of the HAp ceramic structure. In accordance with one embodiment of the invention, the biodegradable polymer is a ploy L-lactic acid polymer, which is formed by enzymatic polymerization catalyzed by a lipase.

Another aspect of the invention relates to methods for preparing a HAp ceramic material. A method in accordance with one embodiment of the invention includes preparing a porous HAp ceramic containing pores having an average pore diameter of 10 μm or larger; and forming a biodegradable polymer in the pores of the porous HAp ceramic. The porous HAp ceramic may be prepared by: preparing a slurry comprising HAp fibers and heat-degradable particles in a selected solvent; filtering the slurry to obtain a paste; preparing a molded body using the paste; compacting the molded body to produce a green compact; and firing the green compact at a temperature at least 1000° C. to produce a porous HAp ceramic structure.

An object of the invention is to provide a calcium phosphate porous body which more effectively promotes bone growth, and a method of manufacturing the porous body.

To solve the above problems, the present invention proposes the following measures.

A calcium phosphate porous body of the present invention formed by intertwining calcium phosphate fibers comprises;

a plurality of first pores formed where the calcium phosphate fibers intersect, and a plurality of equal-diameter substantially spherical second pores with a larger inside diameter than the first pores.

The calcium phosphate porous body of the present invention preferably further comprises a plurality of equal-diameter substantially spherical third pores with a larger inside diameter than the first pores and a smaller inside diameter than the second pores.

The calcium phosphate porous body of the present invention preferably further comprises first connecting channels which interconnect the second pores.

The calcium phosphate porous body of the present invention preferably further comprises second connecting channels which connect the second pores and the third pores.

The calcium phosphate porous body of the present invention preferably further comprises third connecting channels which interconnect the third pores.

In the calcium phosphate porous body of the present invention, the fibrous calcium phosphate is preferably composed of β-tricalcium phosphate.

In the calcium phosphate porous body of the present invention, the fibrous calcium phosphate may be composed of HAp.

The method of manufacturing the calcium phosphate porous body of the present invention comprises: a mixing step for producing a mixture by dispersing, in a solvent, fibrous calcium phosphate, a plurality of first beads which have a first diameter and are burned out by heating, and a plurality of second beads which have a second diameter larger than the first diameter and are burned out by heating; a molding step for molding the mixture; and a firing step for firing the molded mixture at or above the temperature at which the first beads and the second beads are burned out.

The mixing step preferably produces a slurry from the mixture, and the molding step preferably removes the solvent from the mixture and produces a gel.

The manufacturing process also preferably comprises a pressurizing step for pressurizing the molded mixture after the molding step and before the firing step.

Furthermore, preferably the first diameter is an average particle size of 10 to 30 μm, and the second diameter is an average particle size of 100 to 300 μm.

Moreover, in the mixing step, one or both of the first beads and the second beads may be subjected to surface roughening before being be mixed with the fibrous calcium phosphate.

This surface roughening is preferably performed by heating one or both of the first beads and the second beads.

The calcium phosphate porous body of the present invention and method for manufacturing the same can further promote bone growth, and is well suited for use as an ingredient in composite materials used for bone repair or replacement.

Other aspects and advantages of the invention will be apparent from the following description and the appended claims.

BRIEF DESCRIPTION OF DRAWINGS

FIG. 2 shows a flow chart illustrating a method for the preparation of porous HAp ceramic in accordance with a first embodiment.

FIG. 3A shows a porous HAp ceramic prepared without inclusion of carbon beads according to a first embodiment.

FIG. 3B shows porous HAp ceramics prepared with inclusion of carbon beads having diameters of about 150 μm in accordance with a first embodiment.

FIG. 11 (B) shows a partial enlargement of FIG. 11 (A).

FIG. 23 (B) is a Kusabira Orange fluorescence image of the same region.

FIG. 24 (B) is a Kusabira Orange fluorescence image of the same region.

FIG. 25 (B) is a Kusabira Orange fluorescence image of the same region.

FIG. 26 (B) is a Kusabira Orange fluorescence image of the same region.

FIG. 27 (B) is an image of a cross-section of the β-tricalcium phosphate porous body 6 weeks after implantation in the tibia of the cloned pig.

FIG. 28 (B) is an image of a cross-section of the HAp porous body 6 weeks after implantation in the tibia of the cloned pig.

FIGS. 35 (B), (C), and (D) are images of carbon beads subjected to surface roughening at different temperatures.

DETAILED DESCRIPTION

First Embodiment

Embodiments of the invention relate to bin-ceramic materials that are based on bioactive HAp. The bioactive hydroxyapatite materials in accordance with embodiments of the invention have some mechanical properties similar to those of bones. Some embodiments of the invention relate to HAp and poly-L-lactic acid (PLLA) hybrid materials. The mechanical strength and Young's modulus of these HAp-PLLA hybrid materials are closer to those of the natural bones than HAp. In addition, PLLA is biodegradable and can be resorbed in the body to make space for new bone growth. Some embodiments of the invention relate to methods for preparing and using these hybrid materials.

As noted above, the mechanical strengths and physical properties of HAp are very different from those of natural bones. As shown in Table 1 below, hydroxyapatite has a larger Young's modulus, but lower fracture toughness, as compared with a natural bone. Therefore, HAp is more susceptible to brittle fractures, as compared with a natural bone.

TABLE 1

| | Young's Modulus (GPa) | Fracture Toughness (MPa · m$^{1/2}$) | Bending Strength (MPa) |
|---|---|---|---|
| HAp | 86-120 | 0.7-1.2 | 80-250 |
| Cortical Bone | 7-30 | 2-6 | 50-150 |

Figure 1:
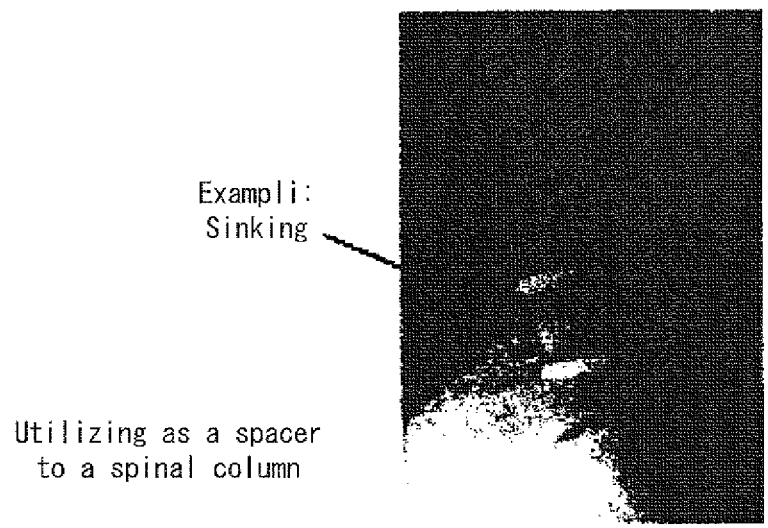
FIG. 1 shows a conventional HAp implant in a spine, illustrating the sinking of bone according to a first embodiment.

Because hydroxyapatite is less flexible and more easily fractured, if HAp is used in bone replacement or repair, unusual stress may develop at the bone-HAp interfaces. Such stress may cause the interfaces to deteriorate overtime, or it may even trigger biological responses that leads to bone loss around the stress interfaces. As a result, the bone replacements may not function properly over time. For example, FIG. 1 shows an example, in which a hydroxyapatite piece is used as a spacer in a spinal column. Over time, the bone and HAp junction deteriorates, resulting in bone sinking.

To overcome the problems described above, it would be desirable to have HAp ceramic materials that have properties similar to those of natural bones. In this regard, inventors of the present invention have previously reported that the properties of porous HAp can be altered by inclusion of other materials in the pores of the HAp structures. For example, when poly(methylmethacrylate) (PMMA) is introduced into porous HAp, it was reported that the hybrid material has a Young's modulus of about 63 GPa, a fracture toughness of about 2 MPa·m$^{-1}$, and a bending strength of about 65 MPa. See, Aizawa et al., Bioceramics, vol. 12, p. 453 (1999); and Aizawa et al., Key Engineer. Mater, vol. 218-220, p. 465-468

(2002). Although PMMA is relatively well tolerated in vivo, PMMA is not biodegradable, and, therefore, the pores in HAp ceramics are permanently blocked.

Some embodiments of the invention relate to porous HAp ceramics that include biodegradable polymers. Such hybrid materials have the desired mechanical properties that are similar to the properties of natural bones. In addition, the biodegradable polymers can be degraded and absorbed to make room for new bone growth.

FIG. 2 shows a flow chart illustrating a method of the invention for preparing a hybrid of HAp and a biodegradable material. In this example, the biodegradable is poly-L-lactic acid (PLLA). However, one skilled in the art would appreciate that other suitable biodegradable materials may be used instead.

As shown in FIG. 2, a slurry of HAp fibers and carbon beads is prepared (step 21). The HAp fibers may be prepared as disclosed in Kawata et al., "Development of porous ceramics with well-controlled porosities and pore sizes from apatite fibers and their evaluations," Journal of Materials Sciences: Materials in medicine, Vol. 15, pp. 817-823 (2004). This paper is referred to as "Kawata publication" in the following description.

For example, HAp fibers may be prepared by precipitation of an aqueous solution containing $Ca(NO_3)_2$ (0.167 mol·dm$^{-3}$), $(NH_4)_2HPO_4$ (0.1 mol·dm$^{-3}$), $(NH_2)_2CO$ (0.5 mol·dm$^{-3}$), and $HNO_3$ (0.1 mol·dm$^{-3}$). This solution contains Ca/P in a ratio of 1.67. This solution is heated at 80° C. for 24 hours and then at 90° C. for 72 hours to produce the HAp fibers having axes about 60-100 μm long. These fibers are collected, for example by filtration. To make a suspension, the HAp fibers are suspended in water at a suitable concentration (e.g., about 1 wt %).

The carbon beads in the slurry may be substituted with any heat-degradable particles. The heat-degradable materials (e.g., carbon beads or plastic beads) will create space between the fibers. After heat treatment, these materials will disappear and leave behind pores within the ceramics. For clarity of description, the following will use carbon beads as examples of the degradable materials. However, one skilled in the art would appreciate that other similar degradable materials (such as plastic beads, etc.) that can leave pores in the ceramics may also be used. Carbon beads are commercially available. For example, Nikabeads® are available from Nippon Carbon Co., Ltd. (Yokohama, Japan) in various diameters (5, 20, or 150 μm).

As shown in the Kawata publication, the sizes of the carbon beads will affect the pore sizes of the final ceramics. For use with embodiments of the invention, carbon beads (or other heat-degradable material beads) of about 10-500 μm in average diameters, preferably about 100-200 μm and most preferably about 150 μm, may be used.

In addition, the amounts of the carbon beads, relative to the amount of the HAp fibers, used will influence the total porosities of the final ceramic. In accordance with embodiments of the invention, a carbon bead to HAp ratio from 1/10 to 50/10 (w/w), preferably from 2/10 to 10/10, more preferably around 5/10, may be used.

Because the carbon beads and the HAp fibers have different densities and tend to separate out in the slurry, it is desirable to add another agent to help disperse these two components (step 22). For example, agar at a suitable concentration (e.g., at 1/10 the amount of the HAp fibers) may be used. With the aid of agar, the fibers and carbon beads can be better dispersed, leading to homogeneous (random) distribution of the pores in the final 3-dimensional ceramic structures. In the absence of agar (or similar suspension aid), the fibers have a tendency to aggregate into a sheet like (2D) structure. The slurry containing agar may be warmed up to a slightly higher temperature (e.g., using a water bath) to help dissolve the agar. One skilled in the art would know how to optimize the amount of agar and what temperature to use without undue experimentation. In addition, materials other than agar may also be used as long as the materials can help with homogeneous dispersion of the HAp fibers and the carbon beads and can be decomposed at high temperature.

To the above slurry (either the HAp slurry or HAp-agar slurry), a co-solvent (such as an alcohol, e.g., ethanol) may be optionally added to change the surface tension of the water solution and to help disperse the particles. The amount of the co-solvent used would depend on the desired effects. For example, when ethanol is used, it may be used at about 10-50% (v/v), preferably about 30% v/v, relative to the total volume (water and ethanol combined volume).

The slurry is used to make green compacts that can be calcined (heated at high temperatures) to make the desired ceramics. For example, the above slurry may be poured into a mold having the desired shape to make a pre-compact. The mold may have a porous or solvent permeable bottom, for example, such that the solvents (e.g., water and ethanol) may be removed, by suction filtration if necessary. In addition to the above described, as noted above, the mixed slurry comprising of HAp fibers and carbon beads can be made more homogeneous by adding a desired amount of agar to the slurry. Agar in the slurry helps to create a homogeneous (random) distribution of pores in the 3D ceramic structure.

The pre-compact body of green compact is allowed to dry. Then, it may be further compacted by applying a selected pressure, for example about 10-50 MPa, preferably about 20-40 MPa, more preferably about 30 MPa, to produce a green compact (step 23). The compaction affects the pore sizes in the final ceramics and may also affect the mechanical strength of the final ceramic products.

The green compact can then be calcined (e.g., fired at high temperatures) to produce the ceramics (step 24). The calcination (heating) may follow conventional procedures. The heating may be performed at a temperature about 1000-1500° C., preferably about 1200-1300° C. The calcination, for example, may be performed in an electrical furnace. Furthermore, in accordance with embodiments of the invention, the heating may be conducted in an atmosphere of steam in order to prevent the loss of hydroxyl groups from the HAp. The time needed for the calcination (heating) would depend on the size of the green compacts, the temperature used, and other factors. Typically, the curing process may take a few hours, for example from 1-10 hours, preferably around 3-5 hours.

The firing (high temperature curing) cures the HAp fibers into ceramics at the same time vaporizes the carbon beads. As a result, the final HAp structures are left with relative large pores (where the carbon beads were), together with small pores that were created by gaps between the fibers (where no carbon beads were incorporated into the green compacts). Thus, these procedures produce HAp structures with bi-modal pore distributions (i.e., with large pores and small pores).

For example, carbon beads having about 150 μm diameters are found to leave pores of about 100 μm or larger in the HAp ceramics. In addition to these pores, the resultant HAp ceramics also contains smaller pores about 1-5 μm diameters that result from the gaps between the HAp fibers that did not include the carbon beads. That is, these porous HAp ceramics actually have pores with two different size distributions: a group of small pores around several micrometers in sizes and another group with pores of about 100 μm or larger in sizes. This may be referred to as "bimodal porous HAp ceramics".

As shown in FIG. 3 panel (A) on the left, the HAp ceramic was made without added carbon beads. As a result, the pores are small in sizes, in the range of a few μm (e.g., 1-5 μm). In contrast, as shown in FIG. 3 panel (B) on the right, the HAp ceramics prepared with the added carbon beads (150 μm diameters) have larger pores (up to 100 μm or larger), in addition to the small pores (1-5 μm), referred to as macro pores and micro pores, respectively, in FIG. 3.

As noted in the Kawata publication, the total porosities of the ceramic products may be controlled by varying carbon bead sizes and the relative carbon bead/HAp amounts. In addition to the carbon beads sizes and amounts, compaction pressure used in making the green compacts and the firing temperatures used in producing the ceramics will also affect the total porosities of the final products. Among these factors, the carbon-bead diameter has the most influence on the final pore sizes, whereas the compaction pressure and the firing temperatures have less impact on the final porosity of the ceramics.

In accordance with embodiments of the invention, the HAp ceramics may have about 30-80% total porosity, preferably have about 40-70% total porosity. By using carbon beads, these ceramics have large pores that are interconnected. These interconnected pores are desirable for inclusion of the biodegradable polymers and also be new growth of bones when used in vivo.

The percentages of pore volumes will affect the physical strength and mechanical properties of the ceramics. Therefore, if stronger or more rigid ceramics are desired, then smaller amount of carbon beads may be used. On the other hand, if more flexible ceramics or ceramics with large total pore volumes are desired, then larger amounts of carbon beads may be used.

Figure 4:
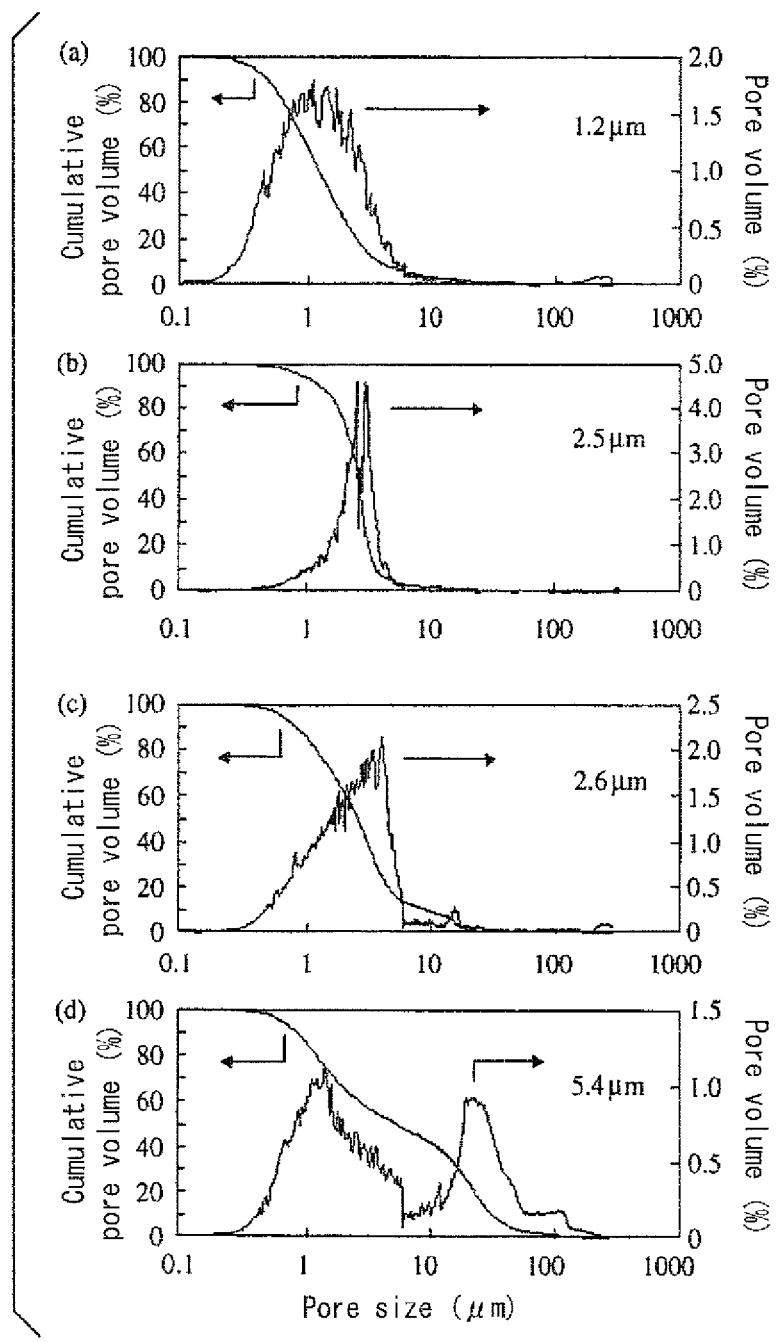
FIGS. 4a-4d show pore-size distributions of HAp ceramics prepared with various carbon beads having different diameters according to a first embodiment.

FIG. 4 shows pore-size distributions and pore volumes of HAp ceramics prepared with different sizes of carbon beads. As shown in FIG. 4, panel (a), when no carbon beads are included, the resultant ceramics have mostly small pores (those arising from gaps between fibers, the median pore diameter is 1.2 μm). When carbon beads (5 μm) are includes, the resultant ceramics have two populations of pores (Panel b; median pore diameter 2.5 μm). When carbon beads of 20 μm diameters are included, the resultant ceramics have pores shifted to larger pore sizes (Panel c; median pore diameter 2.6 μm). FIG. 4, panel (d) shows the ceramics with carbon beads of 150 μm diameters included have a median pore diameter of 5.4 μm. However, these ceramics have two populations of pore sizes, one of which have pores of less than 10 μm sizes, while the other clearly shows pore diameter distribution between 10 and 100 μm.

As noted above, the HAp porous ceramics prepared with inclusion of carbon beads (e.g., 150 μm diameters) may have large pores with diameters on the order of about 100 μm (see FIG. 3 and FIG. 4d). The large pore sizes result in many connected channels in the porous HAp ceramics. Such connected channels are desirable because they facilitate the inclusion of biodegradable polymers in such ceramics, according to embodiments of the invention described below. In addition, these connected channels would also facilitate the formation of bone tissues inside the ceramic after such devices are implanted in a patient.

The ceramic product may be further worked on (e.g., cut or polishing) to produce the final desired ceramic products. The further working step may produce a ceramic product in a shape for the intended use.

Referring again to FIG. 2, in accordance with embodiments of the invention, the porous HAp ceramics may be further modified by inclusion of one or more biodegradable materials in the pores (especially, the connected channels formed by these pores) (step 25). Examples of suitable biodegradable materials may include polyesters, polyamides or the like. In accordance with embodiments of the invention, the biodegradable materials are preferably polyesters; more preferably, the biodegradable materials are polyesters of naturally occurring acids, such as L-lactic acid, glycolic acid, citric acid, etc. The biodegradable polymers may also be prepared from a mixture of these materials, such as a mixed polymer of lactic acid and glycolic acid. In the following description, poly-L-lactic acid esters (PLLA) are used as examples of such biodegradable materials. However, one of ordinary skill in the art would appreciate that embodiments of the invention may use any suitable biodegradable materials known in the art.

In accordance with some embodiments of the invention, poly lactic acid esters may be incorporated into the pores of porous HAp ceramics by enzyme catalyzed reactions to polymerize the lactic acids. Any suitable enzymes may be used for such polymerization, including lipases. Suitable lipases include lipase CA, lipase PS, or any other suitable lipase. Several lipases are commercially available, such as Amano lipase PS from Burkholderia cepacia that is available from Sigma-Aldrich (St. Louis, Mo.).

Figure 5:
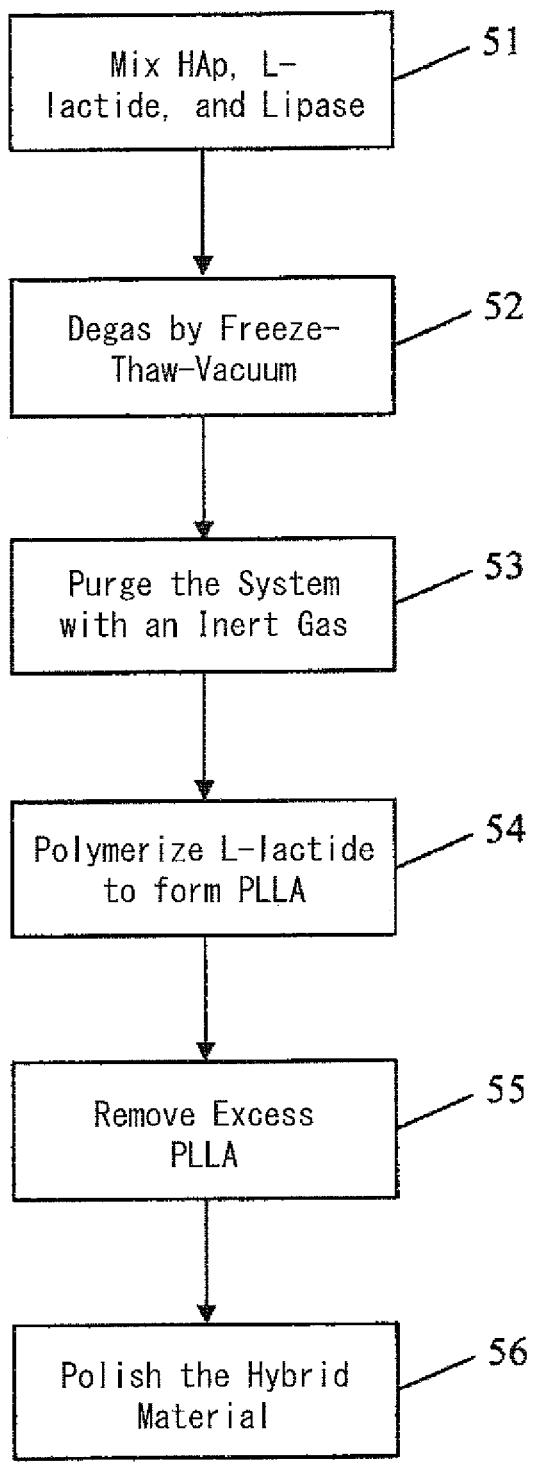
FIG. 5 shows a flow chart illustrating a method for forming a polymer in the pores of a porous HAp ceramic in accordance with a first embodiment.

The polymerization of the lactic acid (or its dimmer, lactide) using an enzyme, such as a lipase (e.g., lipase S), is known in the art. See for example, H. Uyama, K. Takeya, S. Kobayashi, Bull. Chem. Soc. Jpn., 68, 56 (1995). In accordance with embodiments of the invention, PLLA formation can be performed using any suitable protocol and under any suitable conditions. For example, FIG. 5 shows a flow chart illustrating one method for polymerizing lactic acids inside the pores of HAp ceramics in accordance with one embodiment of the invention. As shown in FIG. 5, the HAp, lactic acid (or lactide), and lipase are mixed in a reaction container (step 51).

The substrate and enzyme mixture may be mixed in a solvent (e.g., buffer) that is suitable for the selected lipase. In alternative methods, the substrate (e.g., lactide) solution and the enzyme solution may be separately soaked into the porous HAp ceramics. For example, one may soak the HAp ceramic with the enzyme solution first and allow it to dry (or removing the solution from the pores) after some time for the enzyme to associate with the surface of pores in the ceramic. Then, the resultant ceramic is soaked in a solution containing the substrate (e.g., lactide).

The mixture is degassed by freeze-thaw and vacuuming, which may be repeated 2 or 3 times (step 52). The degassing step is to ensure that the air trapped in the pores within the ceramic is removed and replaced with the reaction solution. The reaction container is then flushed with an inert gas, e.g., nitrogen or argon (step 53). For ease of operation of the freeze-thaw-vacuum cycles, the solution (and the subsequent reaction) may be performed in a reaction vessel having outlets that have valves to facilitate the evacuation of gas and the introduction of the inert gas.

Then, the polymerization is allowed to proceed by keeping the reaction mixture at a proper temperature for a selected duration (step 54), which may depend on the enzyme and reaction conditions used. The commercial suppliers of the lipases often recommend conditions to be used for the reaction. One may follow those recommendations or experiment to improve the efficiency for the particular reaction. Optimization of such reaction is a common practice in the art.

In some experiments, the PLLA polymerization was performed using lactide and lipase at a temperature higher than 100° C. (such as 130° C.) for a selected duration (e.g., 168 h). At this high temperature, the system is under pressure because of the closed reaction container. The high pressure may help force the reaction solution into the pores in the ceramics. Under this condition, the enzyme may not be stable for long. Nevertheless, the inventors found the high temperature conditions to produce good polymerizations. Although the actual mechanisms are not known, it is possible that some or most of the polymerizations may occur without enzyme catalysis under this condition. For example, it is possible that the lipase in the system catalyzes the reaction in the beginning. Once the lactide molecules start to polymerize, each molecule will generate a free hydroxyl group, which can in turn react with another lactide molecule. Thus, the polymerization reaction may proceed in a chain reaction like manner even after the lipase loses activity at high temperature.

After polymerization, the excess PLLA formed is removed (step 55). Then, the HAp-PLLA hybrid may be polished to provide a final product (step 56). Note that the method shown in FIG. 5 is for illustration only. One skilled in the art would appreciate that other variations or modifications of this procedure are possible without departing from the scope of the invention.

Figure 6:
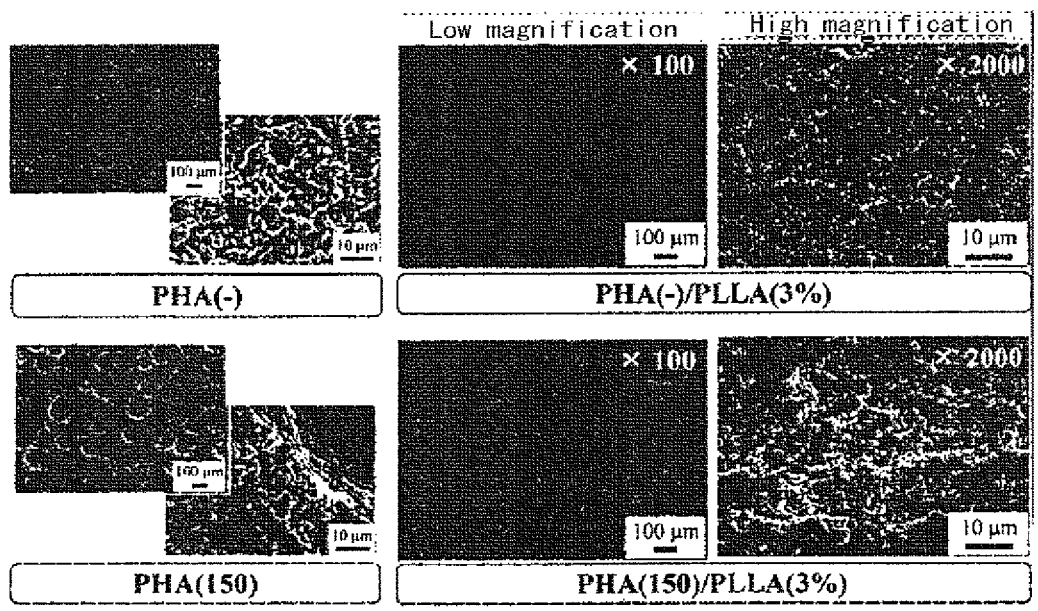
FIG. 6 shows microstructures of HAp and PLLA hybrid materials in accordance with a first embodiment.
Figure 7:
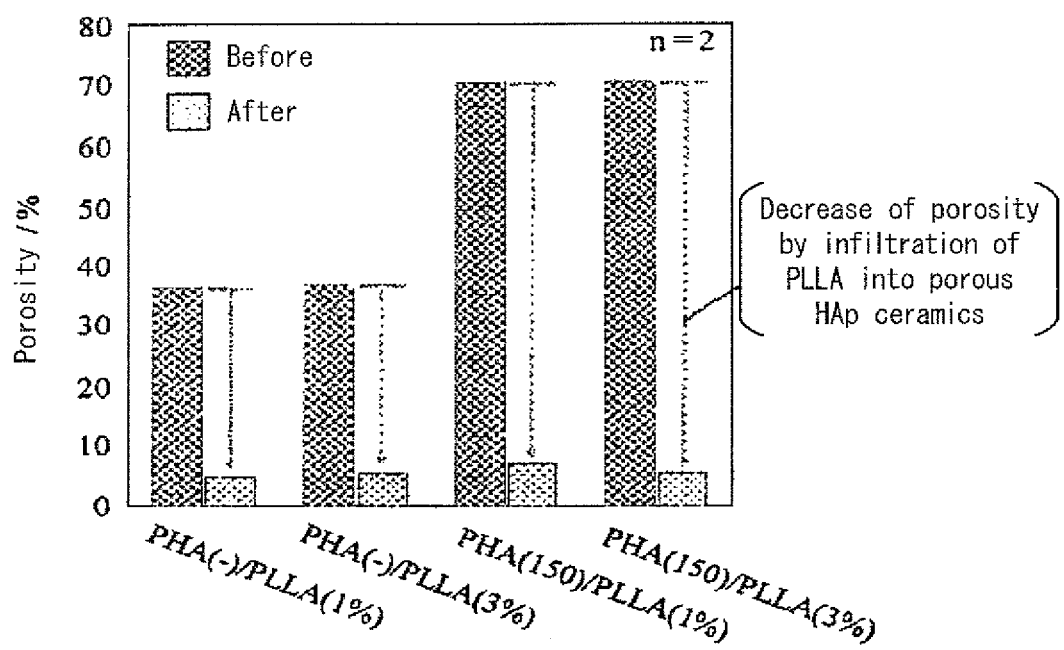
FIG. 7 shows porosity of various HAp-PLLA hybrid materials according to a first embodiment of the invention.

The porous HAp having biodegradable polymers (e.g., poly-L-lactic (PLLA)) included therein are hybrid materials, which include the HAp ceramic parts and the biodegradable material (e.g., PLLA) parts. Because PLLA fills the pores of the HAp ceramics, the cross section of the resulting hybrids changed from a porous appearance to a dense structure, as shown in FIG. 6 and FIG. 7. In these figures, PHA(–) indicates HAp ceramics without carbon beads added during the preparation, while PHA(150) indicates carbon beads of 150 µm average diameters were added. In addition, PLLA(x %) indicates the x % of lipase (relative to the amount of lactic acid in lactide as 100%) used in the polymerization of PLLA.

FIG. 6 shows scanning electron microscope (scanning EM) images of cross sections of various ceramic (without PLLA) and hybrid (with PLLA) materials. As shown in the left panel in FIG. 6, PHA(–), which is HAp ceramic prepared without carbon beads added therein, includes only small pores (arising from intertwines of HAp fibers) (see also FIG. 3). In contrast, PHA(150), which is prepared with carbon beads (150 µm diameters) added to HAp fibers, has both large (around 100 µm in sizes) and small pores (around a few 1 µm in sizes).

As shown in the right panel in FIG. 6, after formation of biodegradable materials (i.e., PLLA) in the pores using 3% lipase (relative to the amount of lactic acid in lactide), the PHA(–)/PLLA(3%) hybrid shows that most pores are filled with PLLA, as evidenced by smoother cross section surface under the microscope. Similarly, the PHA(150)/PLLA(3%) hybrid no longer has large pores (right panel in FIG. 6), and its cross section is mostly smooth, indicating efficient formation of PLLA in the large pores. In both cases, there are only residual amount of small pores not completely filled in.

FIG. 7 shows a graph illustrating quantitative results of the fillings of PLLA in the ceramic pores. From the chart, it is clear that the HAp ceramics prepared without carbon beads added therein have about 38% total porosities, while those prepared with 150 µm carbon beads have about 70% porosities. After formation of PLLA in the pores, all the hybrid materials have about 5-7% remaining pores. This result suggests that the 5-7% remaining pores are common in all ceramics, regardless of how they were prepared. Furthermore, this result suggest that all large pores in the HPA(150) ceramics are completely filled with PLLA because they also have only 5-7% remaining pores. The results shown in FIG. 7 also suggest that whether the polymerization was carried out with 1% or 3% lipase did not make much difference.

Figure 8:
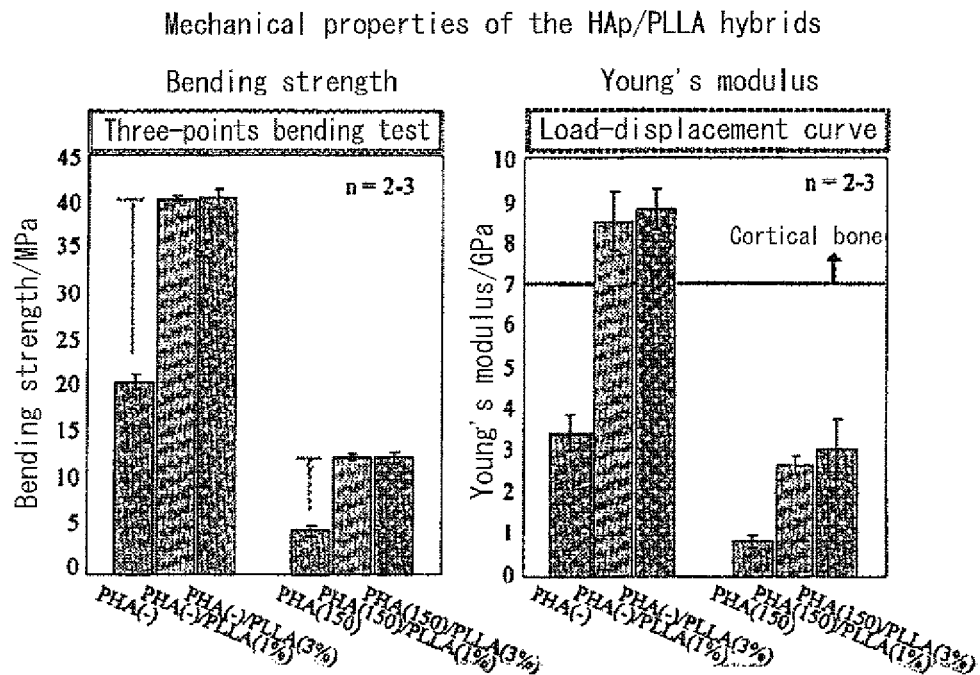
FIG. 8 shows bending strength and Young's modulus of various HAp-PLLA hybrid materials according to a first embodiment of the present invention.

The mechanical or physical properties of HAp ceramics or HAp-PLLA hybrids with large pores are expected to be significantly changed, as compared to small pore HAp ceramics or HAp-PLLA hybrids. As shown in FIG. 8, the bending strengths and Young's modulus of HAp with large pores are much smaller than those without large pores. PLLA formation significantly increases the bending strengths and Young's modulus in both small pore HAp and large pore HAp ceramics. Whether the PLLA polymerization was carried out with 1% or 3% lipase does not seem to make much difference.

The results in FIG. 8 clearly suggest that PLLA formation can be used to improve the bending strengths and Young's modulus of large pore HAp ceramics, making them more closely resemble the physical properties of the natural bone. The inventors have found that large pores in HAp ceramics are important for inducing bone growth in the ceramics (see the discussion below with reference to FIG. 9). However, the presence of large pores in the HAp ceramics significantly lowers the physical strengths of the HAp ceramics, as compared to the HAp ceramic without the large pores. Therefore, PLLA formation provides a viable approach to improve the usefulness of the HAp ceramic materials.

The lower bending strength and Young's modulus of HAp-PLLA hybrids with large pores in accordance with embodiments of the invention render these materials more flexible, as compared to small pore HAp. These large pore HAp-PLLA hybrid materials are intended for applications in which new bone formation is desired. Therefore, the lower physical strengths of these materials will only have temporary impacts. Once new bone growth is achieved, this disparity in physical properties will disappear. Importantly, the hybrids with large pores can facilitate in-growth of bone cells (e.g., osteoblasts) in the interconnected large pores. Therefore, the large pore HAp-PLLA hybrid materials will find applications in situations where new bone formation is desirable.

As shown in FIG. 8, in all cases (HAp ceramics with or without large pores), the inclusion of PLLA increases the mechanical strengths (e.g., bending strength and Young's modulus) of the ceramic materials by a factor of 2 or more. These results validate the concept of using biodegradable materials to alter the mechanical properties of HAp ceramic materials. Furthermore, these results indicate that one can control the pore sizes and/or the degree of biopolymer formation to achieve a desired combination of properties. For example, one may use smaller carbon beads (e.g., 20, 50, or 100 µm diameters) to produce porous ceramics with smaller pores that are still large enough for bone infiltration, while keeping the mechanical properties of the HAp-PLLA hybrid materials closer to those of the natural bone.

The HAp-PLLA hybrid materials incorporate the desired biocompatibility of HAp and the biodegradability of PLLA. These materials when used in vivo are expected to have great biocompatibility and the biodegradable PLLA is expected to give way to incoming bone cells, e.g., osteoblasts. Therefore, these materials are expected to be conducive to new bone tissue formation in the pores of the hybrid materials.

To test the biocompatibility and the utility of HAp-PLLA hybrid materials of the invention, these materials were incubated with MC3T3-E1 cells, which are derived from mouse head bone and have been well characterized as osteoblast-like cells. The incubation was performed in α-MEM culture medium containing 10% fetal calf serum, at 37° C., 5% $CO_2$. Briefly, a piece of the hybrid material (about 15.5 mm diameter, 1-1.5 mm thick) is incubated with $3.0 \times 10^4$ MC3T3-E1 cells and monitored for several days. The materials are removed at different times and assessed with scanning EM to see the growth and attachment of the cells over time.

Figure 9:
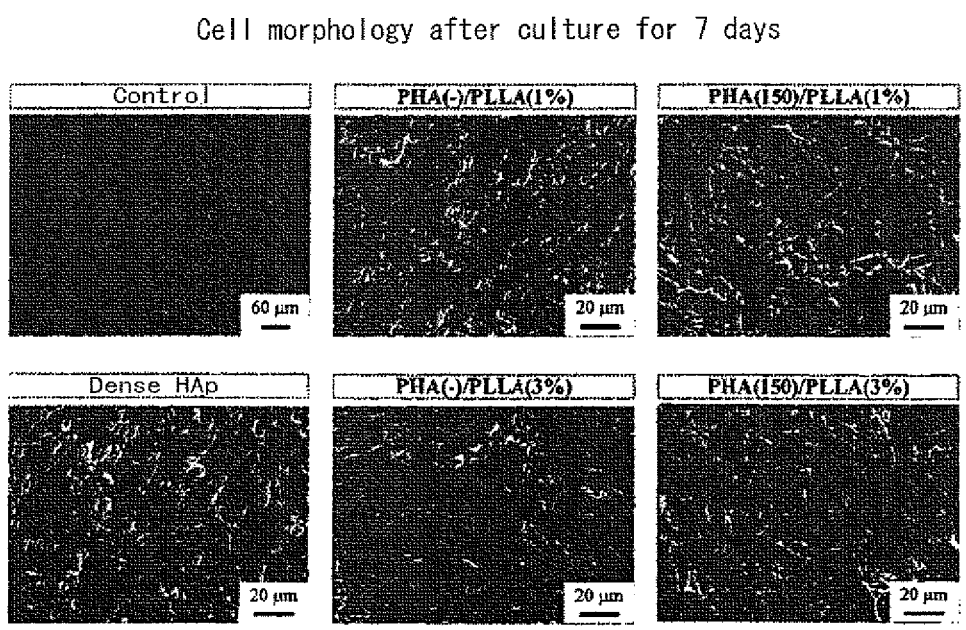
FIG. 9 shows morphology of cells cultured on the HAp-PLLA hybrid materials in accordance with a first embodiment of the invention for 7 days, together with dense HAp ceramics as a positive control and polystyrene for cell culture plate (Control).

As shown in FIG. 9, the HAp-PLLA hybrid materials in accordance with embodiments of the invention indeed can induce cell growth in the pores that were originally occupied by the biodegradable PLLA. As shown, after 7 days, cells grew in the pores of these materials after resorption of the biodegradable materials. These results indicate that the HAp-PLLA hybrid materials of the invention are non-toxic to the cell and they are conducive to the growth of osteoblast-like cells. Therefore, the HAp-PLLA hybrid materials of the invention would be useful in bone repair and replacement.

The utility of these materials in bone repair and replacement is further tested in vivo by implanting these porous ceramics in rabbit tibia. In these experiments, three rabbits each were used to compare the porous ceramics of this invention with a commercially available ceramic, Apaceram®, (from Pentax Corp. Japan). Apaceram® is a biocompatible HAp.

Figure 10:
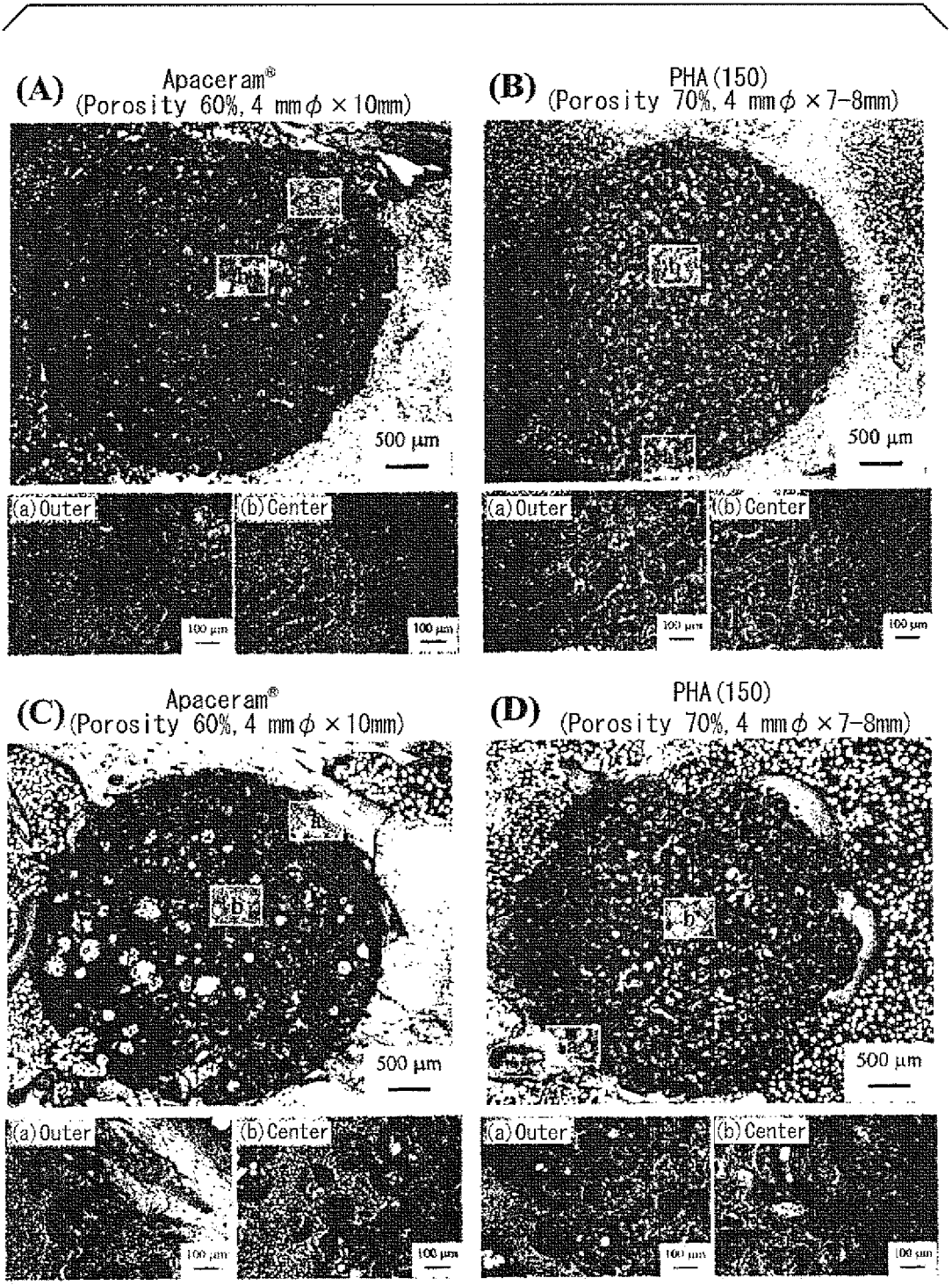
FIGS. 10(A)-10(D) show bone cell growths in the porous ceramics of Apaceram® (FIG. 10(A) and FIG. 10(C)) and bimodal porous HAp ceramics in accordance with a first embodiment of the invention (FIG. 10(B) and FIG. 10(D)) after being implanted into rabbit tibia for 4 weeks (FIG. 10(A) and FIG. 10(B) and 24 weeks (FIG. 10(B) and FIG. 10(D)).

As shown in FIG. 10(A) (Apaceram®) and FIG. 10(B) (bimodal porous HAp of the invention prepared with 150 μm carbon beads; PHA(150)), 4 weeks after implantation, both ceramics show signs of new bone growth, as evidenced by dark blue stainings with toluidine. FIG. 10(C) (Apaceram®) and FIG. 10(D) (bimodal porous HAp of the invention) are after 24 weeks. These results show that the bimodal porous HAp of the invention is comparable or superior to the currently available biocompatible ceramics (Apaceram®) in terms of osteoconductivity, i.e., conducive to new bone formation.

The superior properties of the bimodal porous HAp of the invention is probably attributable to the fact that the large pores are interconnected, which would be more conducive to bone cell growth inside the ceramic. At the same time, the smaller pores may facilitate the delivery of nutrients to the cells.

Advantages of embodiments of the invention may include one or more of the following. The bimodal pore distribution of the HAp ceramics of the invention includes large pores, which form interconnected channels. These interconnected channels facilitate biopolymer formation therein. More importantly, these interconnected channels are conducive to bone growth inside these ceramic materials. The presence of large pores in the HAp ceramics significantly changes the physical properties of these materials. However, by forming PLLA (or other biodegradable) polymers inside these porous HAp ceramic materials, the physical properties of the porous HAp ceramics are greatly improved, rendering these materials having mechanical properties that are more similar to the natural bones. Thus, when these hybrid materials are used in bone repair or replacement, they will not induce as much stress at the interface. In vivo studies have shown that these HAp-PLLA hybrid materials are non-toxic to the cells and are indeed conducive to the growth of bone cells (e.g., osteoblasts).

Second Embodiment

Figure 11:
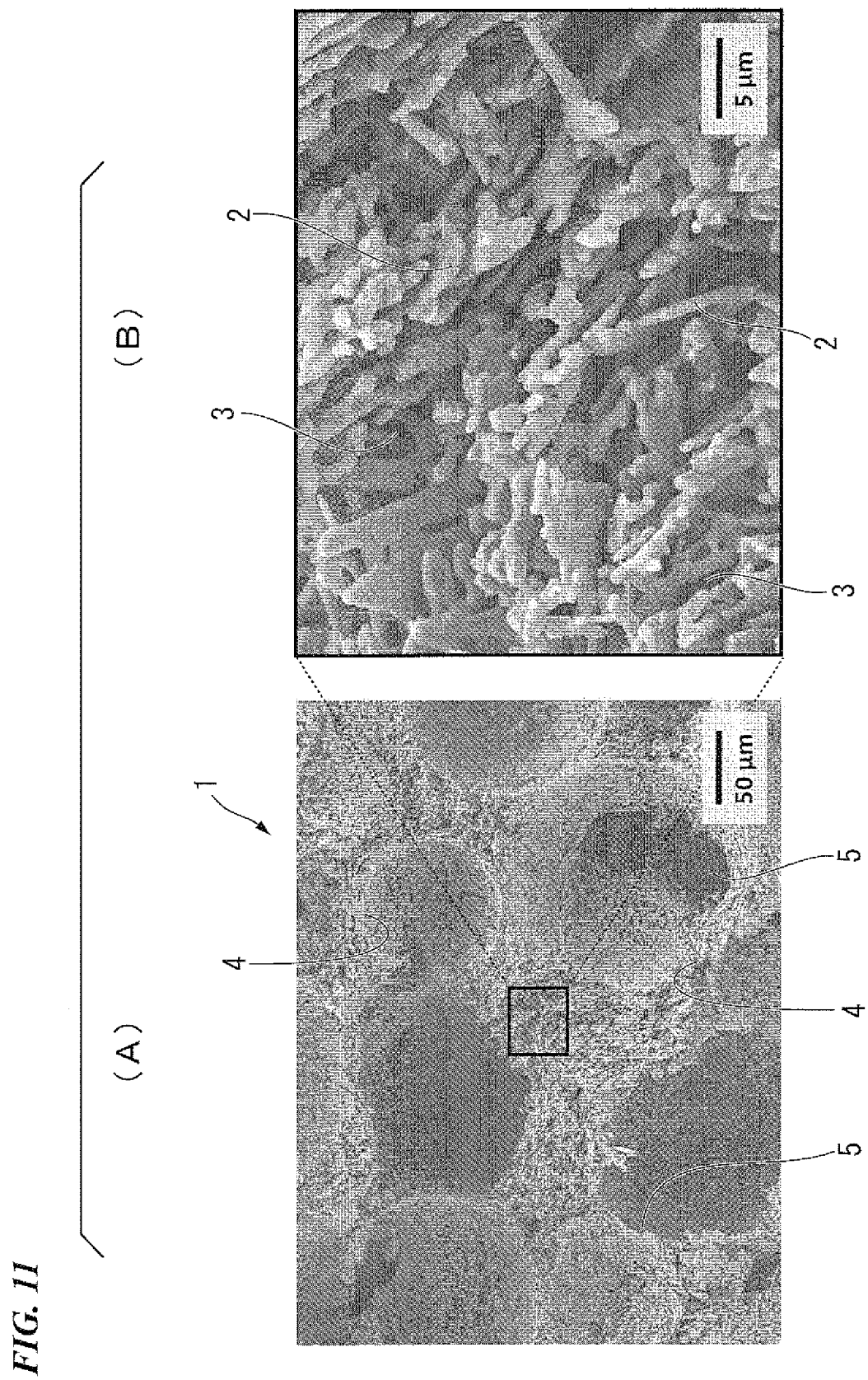
FIG. 11 (A) shows an image of a cross-section of a calcium phosphate porous body according to a second embodiment of the present invention.

A calcium phosphate porous body and manufacturing method according to a second embodiment of the present invention is described below. FIG. 11 is an SEM image of a cross-section of a calcium phosphate porous body 1 according to this embodiment.

Figure 12:
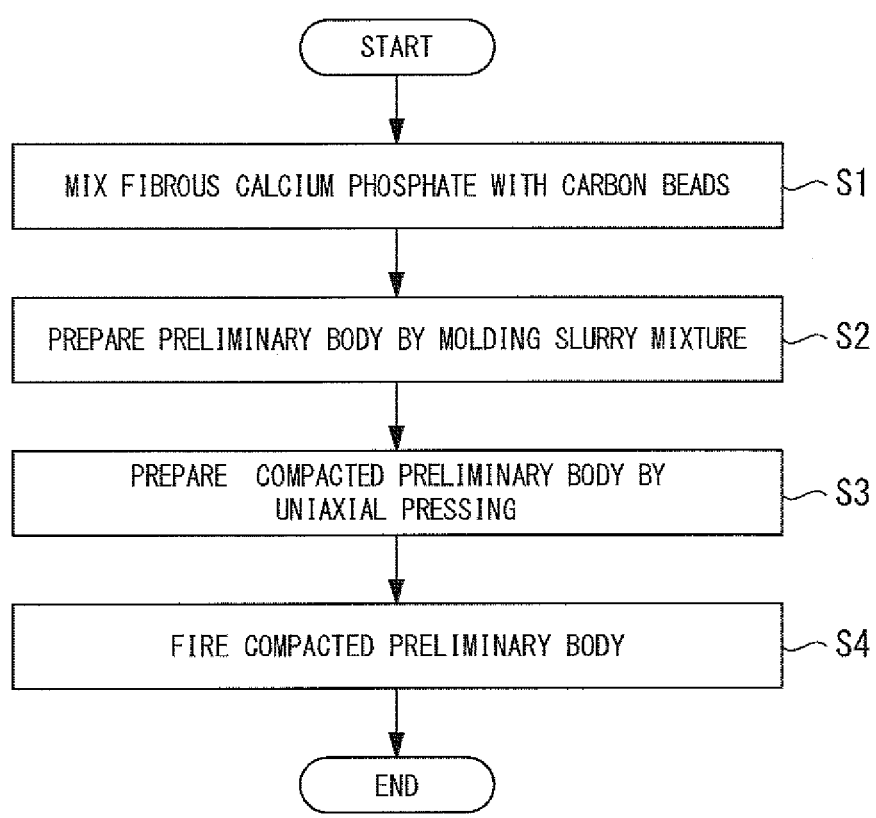
FIG. 12 is a flow chart showing a method of manufacturing the calcium phosphate porous body according to a second embodiment.
Figure 13:
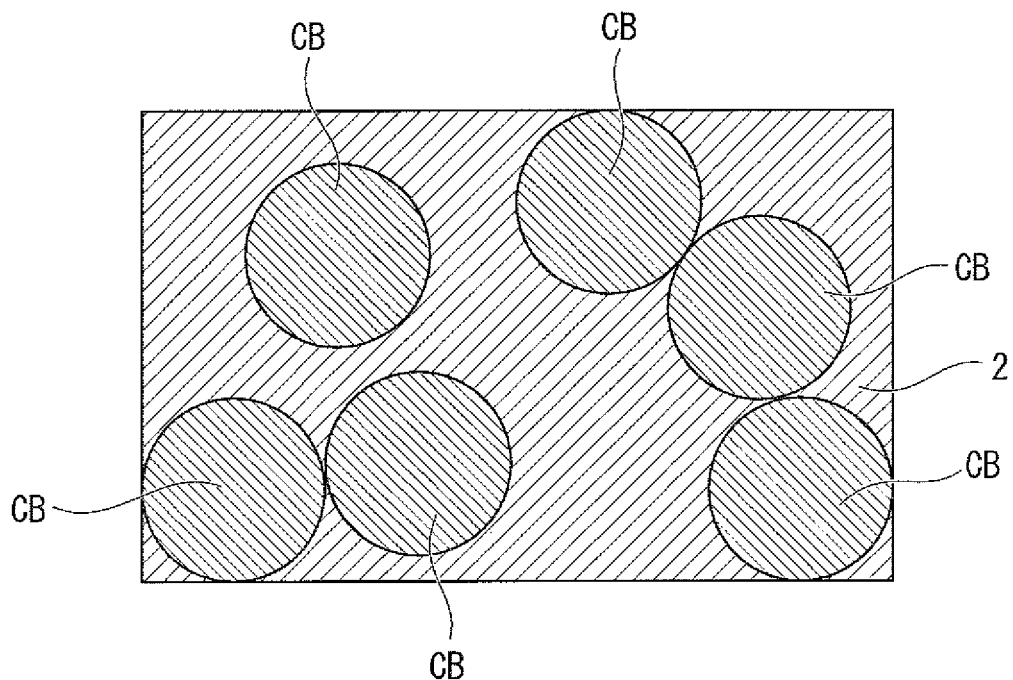
FIG. 13 is an explanatory drawing illustrating a manufacturing step of the calcium phosphate porous body according to a second embodiment.
Figure 14:
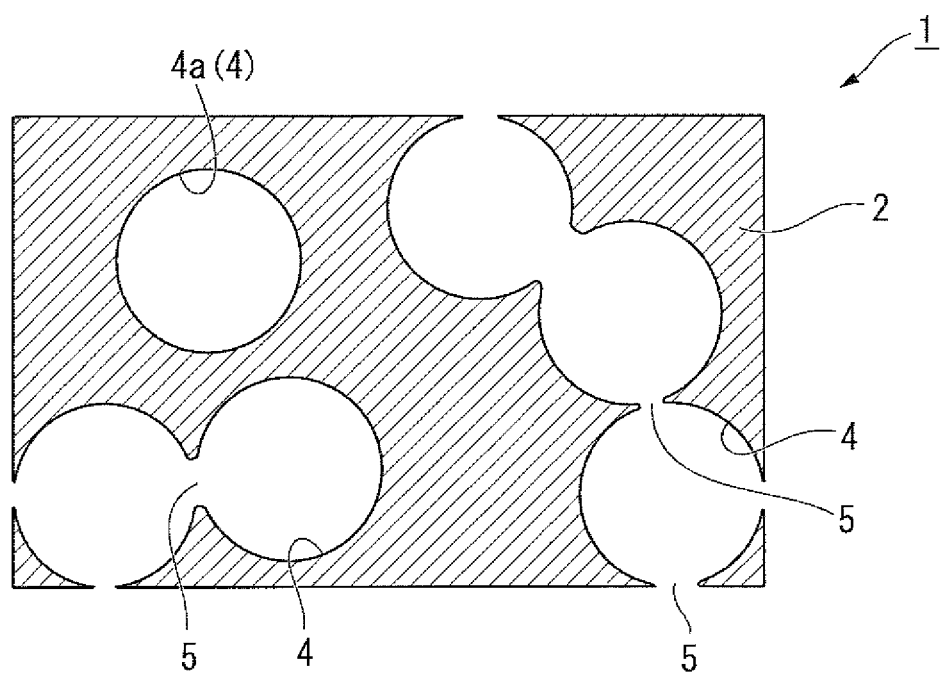
FIG. 14 is an explanatory drawing illustrating a manufacturing step of the calcium phosphate porous body according to a second embodiment.

FIG. 12 is a flow chart showing a method of manufacturing the calcium phosphate porous body 1 according to the present embodiment. FIG. 13 and FIG. 14 are explanatory drawings illustrating a manufacturing step of the calcium phosphate porous body 1.

As shown in FIG. 11 (A), the calcium phosphate porous body 1 is formed by intertwining fibrous calcium phosphate 2 and comprises a plurality of first pores 3 formed by intertwining the fibrous calcium phosphates 2, and a plurality of equal-diameter substantially spherical second pores 4 with a larger inside diameter than the first pores 3. FIG. 11B is an enlargement of the region in the square in FIG. 11A, illustrating the formation of the porous body by the intertwining fibrous calcium phosphates 2.

In the calcium phosphate porous body 1, intertwining of the fibrous calcium phosphates produces an integrated body with gaps of 1 μm to 3 μm between the fibers. These gaps between the fibers are the first pores 3. In the present embodiment, the fibrous calcium phosphate 2 is composed of β-tricalcium phosphate, a highly bioabsorbable material. For example, filling a site of bone loss with β-tricalcium phosphate is known to induce replacement with autologous bone.

The second pores 4 are cavities distributed substantially evenly throughout the calcium phosphate porous body 1. The inside surface shape of the second pores 4 conforms to the shape of the outside surface of the carbon beads CB (see FIG. 13) used in the manufacturing process described later. The carbon beads CB are substantially spherical particles, composed primarily of carbon, which are burned out by heating. In the present embodiment, when manufacturing the calcium phosphate porous body 1, the second pores 4 are formed by loss of the carbon beads CB through heating so that only fired fibrous calcium phosphate 2 remains.

The carbon beads CB (corresponding to the second beads CB2 described later) have a particle size of 50 to 300 μm, preferably have a particle size of 100 to 300 μm, and more preferably have a particle size of 120 to 180 μm.

The maximum inside diameter of the second pores 4 is substantially equal to the diameter of the carbon beads CB. In the present embodiment, the second pores 4 are formed using carbon beads CB with an average particle size of 150 μm to obtain an inside diameter of 150 μm or thereabouts to the second pores 4. The preferred range of the inside diameter of the second pores 4 is 50 to 1000 μm, the more preferred range is 100 to 500 μm, and the most preferred range is 150 to 300 μm.

In this specification, "substantially spherical" refers to spheres for which the ratio (r2/r1) between the major and minor axes is from 1/2 to 1/0.5, preferably from 1/1.5 to 1/0.7, and more preferably from 1/1.1 to 1/0.9.

In this specification, the average particle size is the median size.

Some of the plurality of second pores 4 have first connecting channels 5 which interconnect adjacent second pores 4. The size of the first connecting channels 5 differs according to the distance between the adjacent second pores 4. For example, when the calcium phosphate porous body 1 is manufactured by the method described later, the size of the first connecting channels 5 is within a range from 1 to 50 μm, preferably within a range from 5 to 30 μm, and more preferably within a range from 10 to 20 μm. Depending on the manufacturing conditions, second pores 4 (indicated by reference numeral 4a in FIG. 14), which lack first connecting channels 5 and do not connect to any adjacent second pores 4, may be formed. When the calcium phosphate porous body 1 is used, for example, the calcium phosphate porous body 1 is embedded in the area of a bone defect, the second pores 4 which do not connected to another adjacent second pore 4 is opened to the outside by absorption of the fibrous calcium phosphate 2 into the living body.

Next, a method of manufacturing a calcium phosphate porous body 1 according to the present embodiment is described. In FIG. 12, step S1 is a mixing step in which fibrous calcium phosphate, composed of fibers whose length is within the range from 60 to 200 μm and whose aspect ratio is within a range from 20 to 100, is mixed with carbon beads CB. In step S1, the fibrous calcium phosphate is first suspended in pure water. Next, the carbon beads CB are added to the slurry of suspended fibrous calcium phosphate. Then, 0.1 mass % of agar is added relative to the total mass of the mixed slurry of fibrous calcium phosphate and carbon beads CB. Next, the slurry in which the fibrous calcium phosphate, the carbon beads CB, and pure water are suspended is heated to the temperature at which the agar dissolves. Subsequently, ethanol is added and stirred into the slurry in a 7/3 [v/v] mixing ratio of water to ethanol, and the resulting slurry is cooled to room temperature. By this process, a slurry mixture of the fibrous calcium phosphate and carbon beads CB is prepared. At this point, step S1 is complete and the flow moves to step S2.

Step S2 is a molding step in which molding of the slurry mixture prepared in step S1 is performed.

In step S2, the slurry mixture prepared in step S1 is added in a forming mold at the base of which is a filter whose pore size is smaller than the particle diameter of both the fibrous calcium phosphate and the carbon beads CB, and the liquid component is vacuumed via the filter and removed. By this process, the liquid is removed from the slurry mixture, and the mixture with the liquid removed is molded to a shape that conforms to the inside surface of the forming mold. Then, the mixture with the liquid removed is removed from the forming mold. At this time, the mixture with the liquid removed is rendered a gel by the presence of agar. This mixture removed from the forming mold forms preliminary body molded to the inside surface shape of the forming mold. The forming mold that molds the mixture to a predetermined shape is preferably cylindrical, discoid, or rectangular, and is more preferably cylindrical or rectangular. As shown in FIG. 13, in the preliminary body, the carbon beads CB are enclosed by the fibrous calcium phosphate.

At this point, step S2 is complete and the flow moves to step S3.

Step S3 is a pressurizing step in which uniaxial pressing is performed for the preliminary body produced by Step S2. In step S3, the preliminary body is dried and then subjected to a predetermined compaction pressure (for example 40 MPa in the present embodiment). The higher the compaction pressure applied in step S3, the more strongly the preliminary body is compacted. Thus, increasing the compaction pressure applied in step S3 tends to yield a calcium phosphate porous body 1 with higher mechanical strength by the end of the manufacturing process.

At this point, step S3 is complete and the flow moves to step S4.

Step S4 is a firing step in which firing of the preliminary body pressure-molded in step S3 is performed. In step S4, the compacted preliminary body is heated under air flow at or above the temperature at which the carbon beads CB are burned out. Thus, the carbon beads become $CO_2$ which is released from the preliminary body. The temperature at which the carbon beads are burned out is preferably from 900 to 1,400° C., and more preferably from 1000 to 1,300° C.

At this point, step S4 is complete.

As shown in FIG. 14, the carbon beads CB are eliminated from the preliminary body in step S4, leaving the calcium phosphate porous body 1. As a result of the carbon beads CB being eliminated in step S4, the spaces formerly occupied by the carbon beads CB in the preliminary body become substantially spherical cavities in the calcium phosphate porous body 1. The cavities in the calcium phosphate porous body 1 function as pores (second pores 4) with a diameter of 150 μm or thereabouts into which cells can infiltrate. Furthermore, the gaps formed between intertwined strands of fibrous calcium phosphate 2 function as pores (first pores 3) with a diameter of 1 to 3 μm or thereabouts into which biological fluid and culture medium can infiltrate.

Moreover, connecting channels (first connecting channels 5) with a diameter of 1 to 20 μm are sometimes formed between adjacent second pores 4. The first connecting channels 5 function as channels that allow cells to move from a given second pore 4 to its neighbor.

The second pores 4 into which cells can infiltrate, and the first pores 3 into which biological fluids and culture medium can infiltrate, are distributed substantially evenly throughout the calcium phosphate porous body 1 of the present embodiment. Therefore, cells adhere well to the inside of the calcium phosphate porous body 1, which promotes bone growth.

Furthermore, in the example above, the fibrous calcium phosphate 2, being composed of β-tricalcium phosphate, is highly bioabsorbable and easily replaced with autologous bone. On the other hand, a fibrous calcium phosphate 2 composed of HAp is replaced with autologous bone at a slower rate than β-tricalcium phosphate, allowing the mechanical strength to be maintained in the living body for longer as compared with β-tricalcium phosphate.

Third Embodiment

Figure 15:
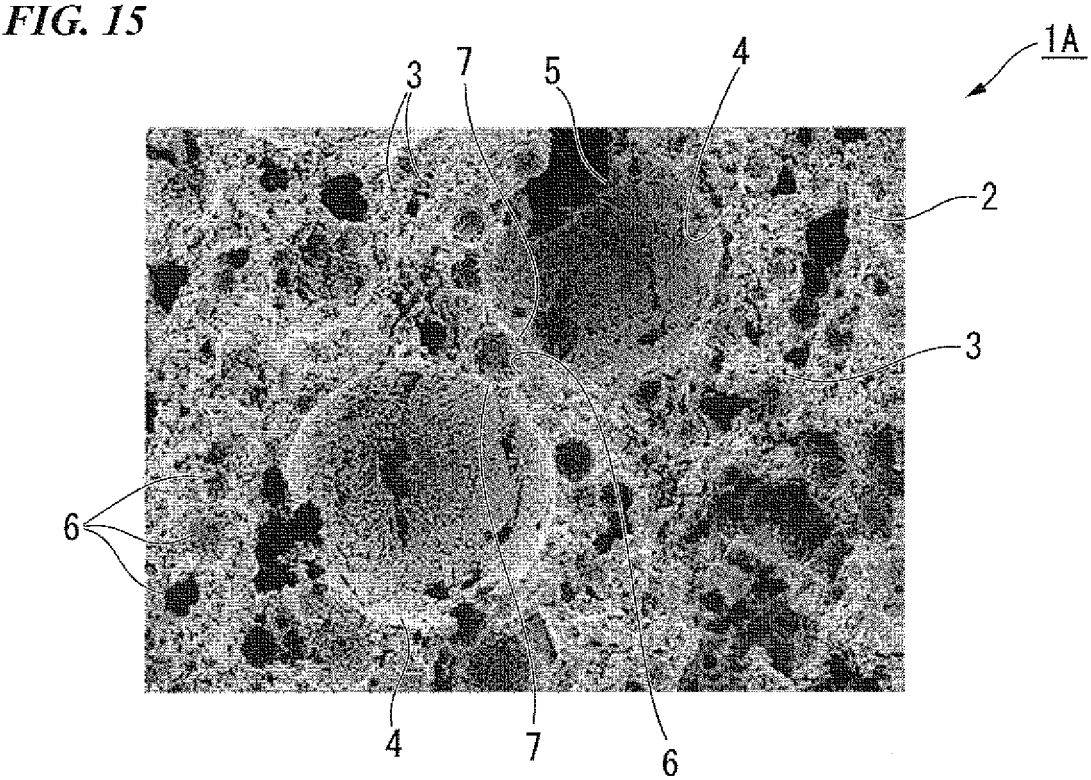
FIG. 15 is an image of a cross-section of a calcium phosphate porous body according to a third embodiment of the present invention.
Figure 16:
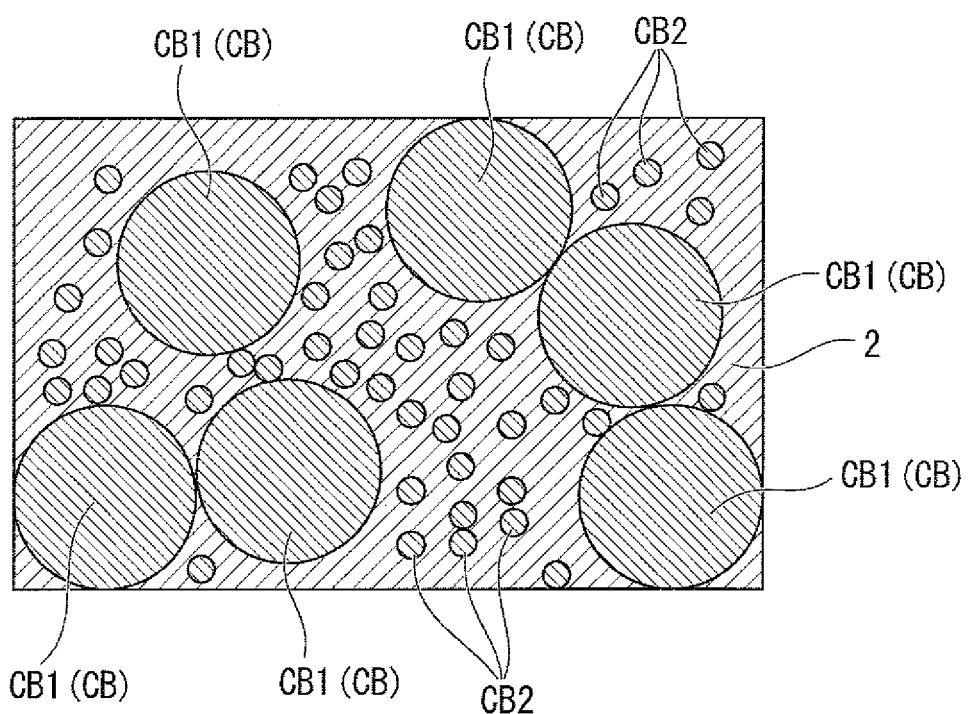
FIG. 16 is a schematic drawing of a preliminary body in a manufacturing step of the calcium phosphate porous body according to a second embodiment.
Figure 17:
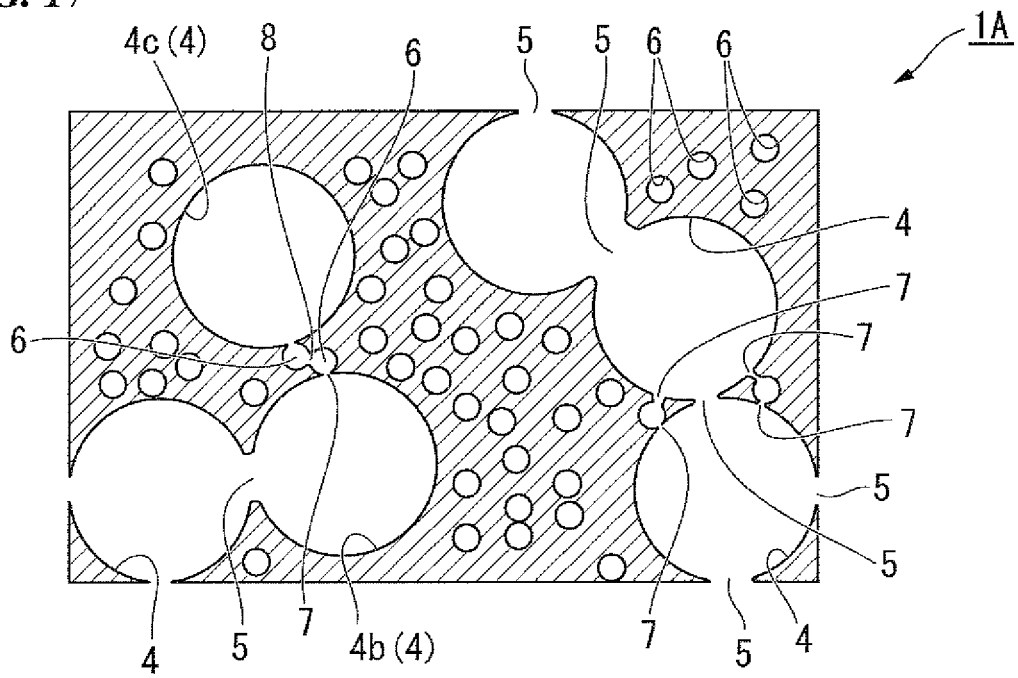
FIG. 17 is a schematic drawing of a fired porous body in a manufacturing step of the calcium phosphate porous body according to a second embodiment.

Next, a calcium phosphate porous body and manufacturing method according to a third embodiment of the present invention is described below. FIG. 15 is an SEM image of a cross-section of the calcium phosphate porous body 1A according to this embodiment. FIG. 16 and FIG. 17 are diagrams explaining the manufacturing process of the calcium phosphate porous body of the present embodiment, wherein FIG. 16 is a schematic drawing of a preliminary body and FIG. 17 is a schematic drawing of the calcium phosphate porous body 1A after firing.

As shown in FIG. 15 and FIG. 17, the calcium phosphate porous body 1A of the present embodiment differs from the calcium phosphate porous body 1 described in the second embodiment by further comprising a plurality of substantially spherical third pores 6 of substantially equal diameter which have an inside diameter larger than the first pores 3 described in the second embodiment and smaller than the second pores 4 described in the second embodiment.

The third pores 6 are cavities distributed substantially evenly throughout the calcium phosphate porous body 1A. The inside surface shape of the third pores 6 conforms to the shape of the outside surface of the carbon beads (first beads CB1, see FIG. 16) used to form the third pores 6 in the manufacturing process described later. The first beads CB1, in the same manner as the carbon beads CB used to form the second pores 4 (called the second beads CB2 to distinguish them from the first beads CB1. See FIG. 16), are substantially spherical particles composed primarily of carbon which are burned out by heating.

The diameter of the first beads CB1 is smaller than that of the second beads CB2, and substantially the same as a cell. Specifically, the average particle size of the first beads CB1 is approximately 10 to 30 μm, is preferably 15 to 25 μm, and is more preferably 18 to 22 μm.

The preferred range of the inside diameter of the third pores 6 is 3 to 50 μm, the more preferred range is 5 to 30 μm, and the most preferred range is 15 to 25 μm.

The third pores 6 are located in the gaps between the plurality of second pores 4, and function as connecting channels which connect isolated second pores 4, or as sites where cells can adhere to promote bone growth.

Furthermore, some of the plurality of third pores 6 have second connecting channels 7 which connect the interiors of second pores 4 and third pores 6. The size of the second connecting channels 7 differs according to the distance between the second pores 4 and the third pores 6. For example, when the calcium phosphate porous body 1 is manufactured according to the manufacturing method described later, the size of the second connecting channels 7 is within a range from 1 to 5 μm. Depending on the manufacturing conditions of the calcium phosphate porous body 1, third pores 6 may be formed that do not connect to an adjacent third pore 6 or a second pore 4. Such third pores 6, in the same manner as second pores 4a (see FIG. 14) which do not connect to another adjacent second pore 4, is opened to the outside by absorption of the fibrous calcium phosphate 2 into the living body.

In addition, as shown in FIG. 17, the calcium phosphate porous body 1A comprises third connecting channels 8 which interconnect a plurality of third pores 6. For example, when third connecting channels 8 are formed in the calcium phosphate porous body 1A, isolated second pores 4 (indicated by reference numeral 4b and 4c in FIG. 17) can be connected via a plurality of third pores 6.

Next, a method of manufacturing the calcium phosphate porous body of the present embodiment is described, focusing on the points that differ from the second embodiment.

In the present embodiment, in step S1 described above (mixing step, see FIG. 12), the first beads CB1 and the second beads CB2 are mixed together to form a slurry. The mixing ratio of the first beads CB1 and second beads CB2 can be set according to the level of strength desired of the calcium phosphate porous body 1A. That is, as the proportion of first beads CB1 with the smaller average particle size increases, the strength of the calcium phosphate porous body 1A decreases. Conversely, as the proportion of second beads CB2 with the larger average particle size increases, cells can more readily infiltrate the calcium phosphate porous body 1A.

Subsequently, the same procedure as steps S2 through S4 of the second embodiment is performed to obtain the calcium phosphate porous body 1A.

As shown in FIG. 16 and FIG. 17, in the present embodiment, the substantially spherical voids formed by loss of the first beads CB1 function as pores (third pores 6) into which cells can infiltrate.

Furthermore, adding the first beads CB1 in addition to the second beads CB2 means the second beads CB2 (equivalent to the carbon beads CB in the second embodiment) can be distributed even more evenly than in the second embodiment. Therefore, the even distribution of second pores 4 is formed to yield a calcium phosphate porous body 1A, into which cells can readily infiltrate and which can promote bone growth.

Moreover, because the third pores 6 formed using the first beads CB1 can interconnect isolated second pores 4, interconnectivity can be increased while maintaining the strength of the calcium phosphate porous body 1A.

Next, the calcium phosphate porous body and manufacturing method according to the second and third embodiments of the present invention are described in more detail based on the following examples.

Example A1

In the present example, the calcium phosphate porous body described in the second embodiment above is manufactured using carbon beads with an average particle size of 150 μm.

(Synthesis of Fibrous Calcium Phosphate)

As the starting material, Wako Pure Chemical Industries special grade calcium nitrate tetrahydrate ($Ca(NO_3)_2 \cdot 4H_2O$), diammonium hydrogen phosphate ($(NH_4)_2HPO_4$), urea ($(NH_2)_2CO$), and nitric acid ($HNO_3$) were used. A sample solution was prepared by mixing 0.167 mol·dm$^{-3}$ of $Ca(NO_3)_2 \cdot 4H_2O$, 0.100 mol·dm$^{-3}$ of $(NH_4)_2HPO_4$, 0.500 mol·dm$^{-3}$ of $(NH_2)_2CO$, and 0.10 mol·dm$^{-3}$ of $HNO_3$, to give a Ca/P ratio of 1.67.

750 cm$^3$ of this sample solution was placed in a 1 liter three-necked round-bottom flask and refluxed for 48 hours at 80° C. When measuring the reaction time, the time when the temperature of the sample solution reached to 80° C. was deemed 0 hour. The sample solution was then subjected to suction filtration, and the solid component obtained by the filtration process was then washed three times in up to 500 cm$^3$ of pure water. Then, 2 mass % of pure water was added to give a calcium phosphate fiber slurry (hereafter "CPF slurry").

(Mixing Step)

Carbon beads with an average particle size of 150 μm (Nikabeads®, Nihon Carbon Company) were added to the CPF slurry in a quantity equivalent to 50% of the mass of the fibrous calcium phosphate in the slurry. In addition, 0.10 mass % of Wako Pure Chemical Industries special grade agar was added to the CPF slurry to which the carbon beads had been added. The mixture of fibrous calcium phosphate, carbon beads, and agar was heated at 60° C. for one hour to melt the agar, after which ethanol was added into the slurry in a 7/3 [v/v] mixing ratio of water to ethanol and stirred. The mixture was then left at room temperature to form a gel.

(Molding Step)

The mixture prepared in the above mixing step was stirred and then poured into a forming mold (PVC tube (16 mm internal diameter) or acrylic mold (inside dimensions 6 mm×45 mm). The liquid (pure water) was then removed from the mixture poured into the PVC tube or acrylic mold by suction filtration. Up to 25 cm$^3$ of the mixture was supplied to the PVC tube, and up to 40 cm$^3$ of the mixture was supplied to the acrylic mold. Finally, the mixture supplied to the PVC tube or acrylic mold was dried, thereby producing a preliminary body in a predetermined shape.

(Pressurizing Step)

The preliminary body was subjected to uniaxial pressing at 40 MPa, to form a disc-shaped preliminary body in the case of the PVC tube, or a flat preliminary body in the case of the acrylic mold. Each preliminary body was approximately 3 mm thick.

(Firing Step)

The preliminary body was fired using a model KTF433N 1500° C. tube furnace made by Koyo Thermo Systems, yielding a calcium phosphate porous body.

In the firing step, the rate of temperature increase was 5° C.·min$^{-1}$, the temperature was maintained for 5 hours after reaching 1,000° C., and the firing environment was under air flow of 300 cm$^3$·min$^{-1}$.

By this series of steps in the present example, the β-tricalcium phosphate porous body described in the second embodiment was obtained.

Example A2

For the β-tricalcium phosphate porous body obtained in example A1, this example illustrates the relationship between the quantity of carbon beads and the porosity of the β-tricalcium phosphate porous body.

In the present example, in the mixing step, carbon beads were added in quantities equivalent to 25%, 50%, 75%, and 100% of the mass of the fibrous calcium phosphate in the CPF slurry. A control experiment was also conducted in which no carbon bead was added. All other steps were the same as in example A1.

Figure 18:
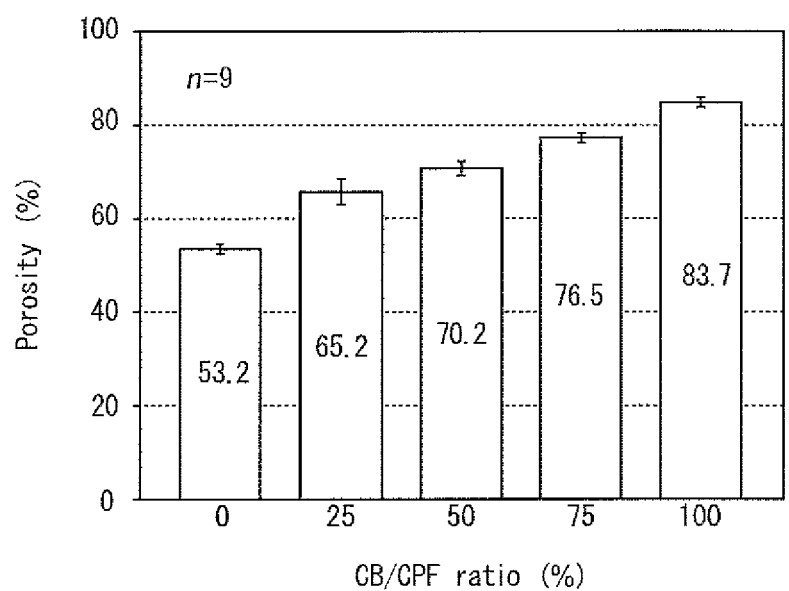
FIG. 18 is a graph showing the relationship between the additive amount of carbon beads and the porosity of the β-tricalcium phosphate porous body, in an example of the calcium phosphate porous body and manufacturing method according to a second embodiment.

FIG. 18 is a graph showing the relationship between the quantity of carbon beads and the porosity of the β-tricalcium phosphate porous body. As shown in FIG. 18, adding the carbon beads increased the porosity of the calcium phosphate porous body. Furthermore, the greater the quantity of the carbon beads, the higher the porosity.

Example A3

This example illustrates the relationship between the quantity of carbon beads and the mechanical strength in the β-tricalcium phosphate porous body obtained in example A2.

Mechanical strength was evaluated by measuring the three point bending strength and Young's modulus. The three point bending strength was measured for the flat β-tricalcium phosphate porous body prepared in example A2 above using a Shimadzu autograph AGF-J (made by Shimadzu Corporation). Table 2 shows the results of measuring the three point bending strength.

TABLE 2

| Crosshead speed | 0.5 mm/min |
|---|---|
| Set load | 50 N |
| Point-to-point distance | 20 mm |
| Distance moved | 10 mm |
| Load cell | 50 N |

The three point bending strength was calculated by Equation 1 below.

[Equation 1]

$$S_b = \frac{3Pl}{2wt^2} \quad \text{Equation 1}$$

In Equation 1 above, $S_b$ is the three point bending strength [Pa], P is the load [N], l is the point to point distance [m], t is the thickness of the test piece [m], and w is the width of the test piece.

The data processing software TRAPEZIUM Ver. 2.2.2 made by Shimadzu Corporation was used to calculate the three point bending strength.

The Young's modulus was calculated from the slope of the load-displacement curve plotted from the three point strength values, using Equation 2 below.

[Equation 2]

$$E_b = \frac{l^3(P_2 - P_1)}{4wt^3(y_{b2} - y_{b1})} \quad \text{Equation 2}$$

In Equation 2, $E_b$ is the Young's modulus obtained by the three point bending test [N/m²], $y_b$ is the net displacement of the load point [m], P is the load [N], t is the thickness of the test piece [m], and w is the width of the test piece [m].

Figure 19:
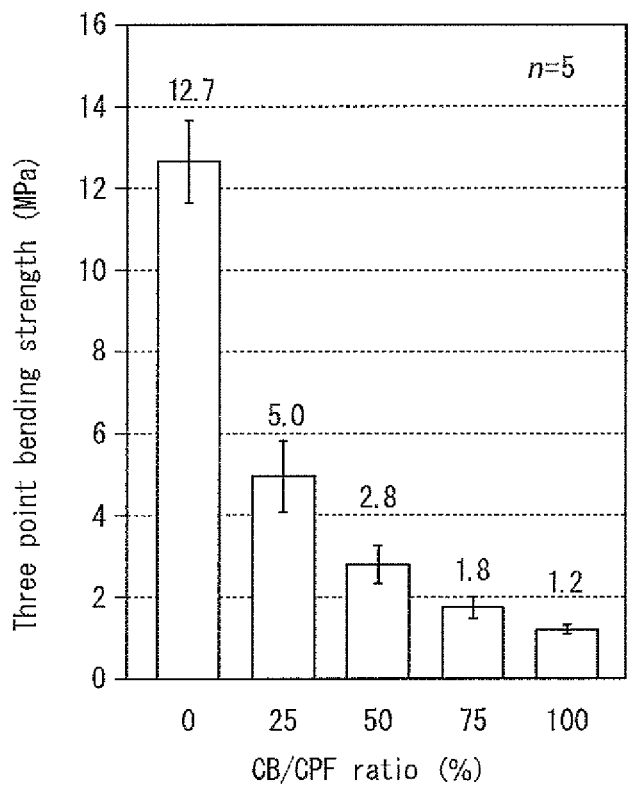
FIG. 19 is a graph showing the three point bending strength calculated for an example of the calcium phosphate porous body and manufacturing method according to a second embodiment.
Figure 20:
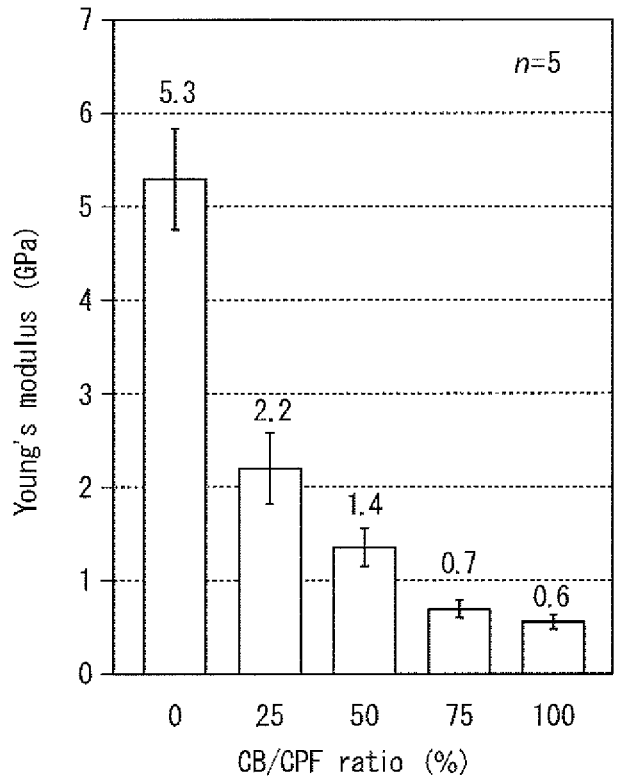
FIG. 20 is a graph showing the Young's modulus calculated for the same example.

FIG. 19 and FIG. 20 are graphs showing the three point bending strength and Young's modulus calculated in the present example. As shown in FIG. 19 and FIG. 20, the three point bending strength and Young's modulus of the β-tricalcium phosphate porous body decrease as the quantity of carbon beads increases.

Example A4

For the β-tricalcium phosphate porous body obtained in example A1, this example illustrates the relationship between the compaction pressure in the molding step and the porosity of the β-tricalcium phosphate porous body.

In this example, the β-tricalcium phosphate porous body according to example A1 above was manufactured with three compaction pressures in the molding step: 30 MPa, 40 MPa, and 50 MPa, and the porosity of the β-tricalcium phosphate porous body at each compaction pressure was measured.

Figure 21:
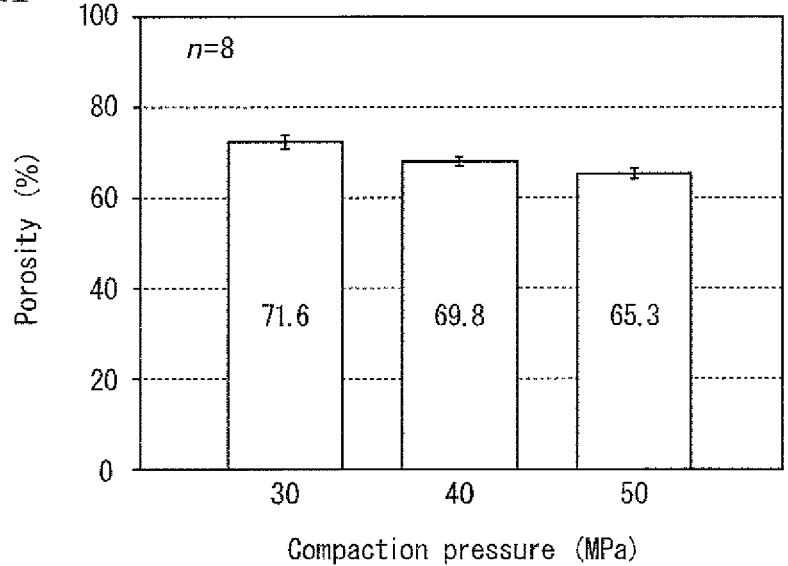
FIG. 21 is a graph showing the relationship between compaction pressure and the porosity of the β-tricalcium phosphate porous body in an example of the calcium phosphate porous body and manufacturing method according to a second embodiment.

FIG. 21 is a graph showing the porosity of the β-tricalcium phosphate porous body at each compaction pressure. As shown in FIG. 21, the porosity of the β-tricalcium phosphate porous body shows a reducing trend as the compaction pressure of the molding step increases.

Example A5

This example illustrates the pore size distribution of the β-tricalcium phosphate porous body manufactured by the steps described in example A1. The pore size distribution of the β-tricalcium phosphate porous body was measured by a mercury intrusion method using a Micrometrics AutoPore IV 9520. Table 3 below shows the measurement conditions of the pore size distribution.

TABLE 3

| Sample shape | Disc (15 mm diameter) |
|---|---|
| Sample weight | 0.5 g (approx.) |
| Initial pressure | 7 kPa (up to 1 psia) |

Figure 22:
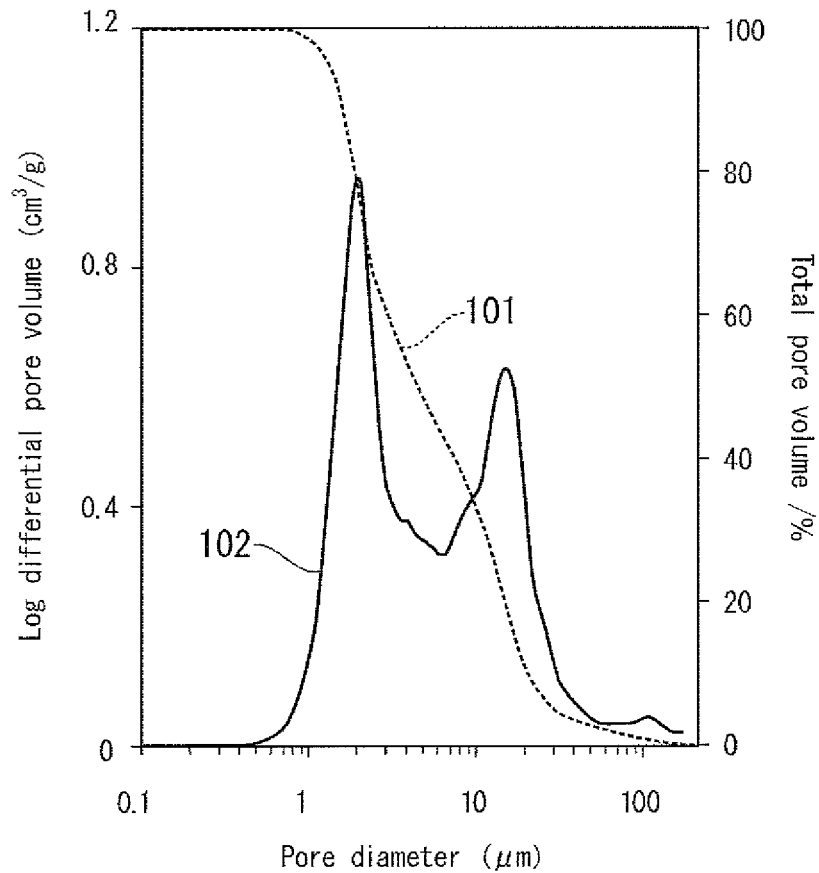
FIG. 22 is a graph showing the relationship between pore diameter and pore volume of the β-tricalcium phosphate porous body in another example of the calcium phosphate porous body and manufacturing method according to a second embodiment.

FIG. 22 is a graph showing the relationship between the pore diameter and pore volume in the β-tricalcium phosphate porous body of the present example. In FIG. 22, the line indicated by reference numeral 101 shows the total pore volume, and the line indicated by reference numeral 101 shows the log differential pore volume.

As shown in FIG. 22, in the present example, the pore size distribution was a curved shape exhibiting three peaks at 1 to 3 μm, about 15 μm, and about 100 μm.

Here, the three peaks at 2 μm, 15 μm, and 100 μm respectively arise from the first pores formed by the intertwined fibrous calcium phosphate, the first connecting channels which connect a plurality of second pores, and the second pores themselves.

Example A6

This example illustrates the results of in vivo evaluation of the β-tricalcium phosphate porous body manufactured according to the steps in example A1 above, with reference to FIG. 23 through FIG. 26.

In contrast to example A1, this example used a cylindrical β-tricalcium phosphate porous body with a diameter of 4 mm and a height of 8 mm.

The cylindrical β-tricalcium phosphate porous body was subjected to dry heat sterilization at 160° C. for 90 minutes, and implanted in the tibia of a cloned pig carrying the Kusabira Orange fluorescence gene (huKO). The test conditions are summarized in Table 4 below.

TABLE 4

| Sample shape | Cylinder |
| Implantation site | Single tibia |
| Duration of implantation | 6 weeks |
| Pig age | 2 years (weight: 200 kg) |
| Pig gender | Male |

After 6 weeks in vivo, the tibia with the implanted β-tricalcium phosphate porous body was extracted, and frozen tissue sections including the β-tricalcium phosphate porous body were prepared using a cryostat microtome (Leica CM3050 S). In addition, the frozen tissue sections were stained, then observed and analyzed using image analysis software (WinROOF by Mitani Corporation).

The frozen tissue sections were stained by HE staining, toluidine blue staining, TRAP staining, and ALP staining. The stained frozen tissue sections were then observed using a biological microscope having phase contrast and fluorescence imaging modes, and images were captured using a microscope camera. In FIG. 23 to FIG. 26, (A) shows the results of staining with the respective staining dyes, wherein the dark areas are the areas stained by the dye. Moreover, in FIG. 23 to FIG. 26, (B) shows the results of fluorescence imaging, wherein the white areas are the areas that exhibit fluorescence.

Figure 23:
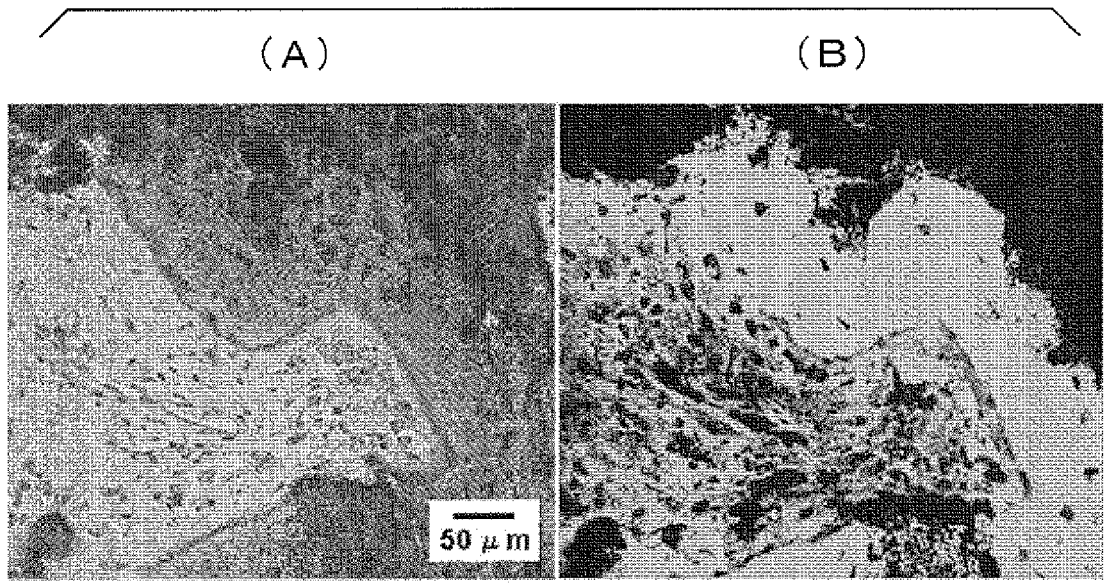
FIG. 23 (A) is an image of an HE stained tissue section.

FIG. 23 (A) is an image of an HE stained tissue section. FIG. 23 (B) is a Kusabira Orange fluorescence image of the same region. As shown in FIG. 23 (A) and FIG. 23 (B), the stain differentiates between the nuclei and cytoplasm. Furthermore, mature bone was stained darker than other cells in the field of view.

Figure 24:
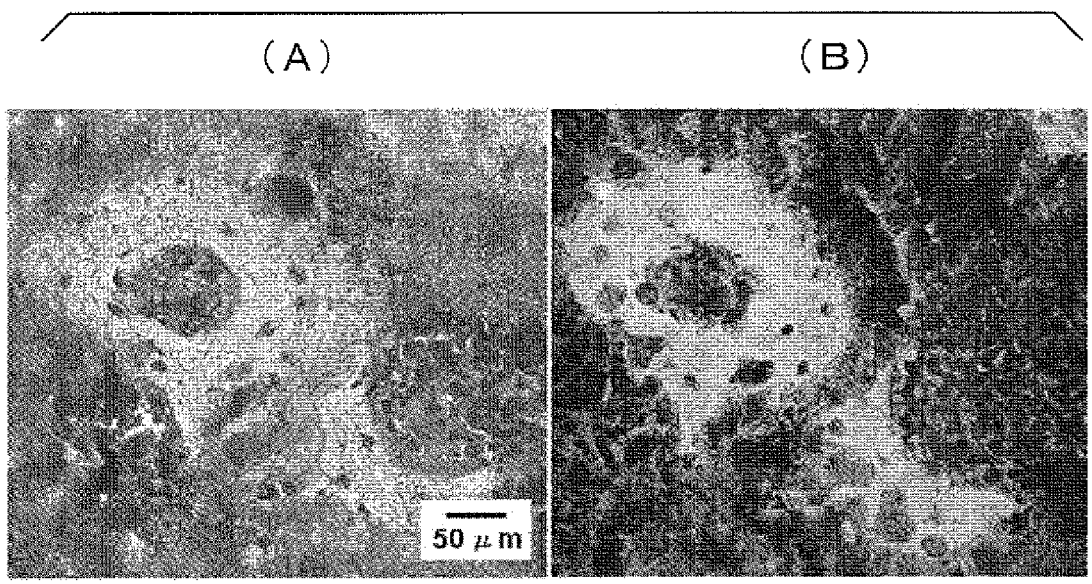
FIG. 24 (A) is an image of a toluidine blue stained tissue section.

FIG. 24 (A) is an image of a toluidine blue stained tissue section. FIG. 24 (B) is a Kusabira Orange fluorescence image of the same region. As shown in FIG. 24 (A) and FIG. 24 (B), a large amount of mature bone was observed along the walls of the second pores at the edges of the β-tricalcium phosphate porous body. Furthermore, significant new growth of immature bone was observed at the center of the β-tricalcium phosphate porous body.

Figure 25:
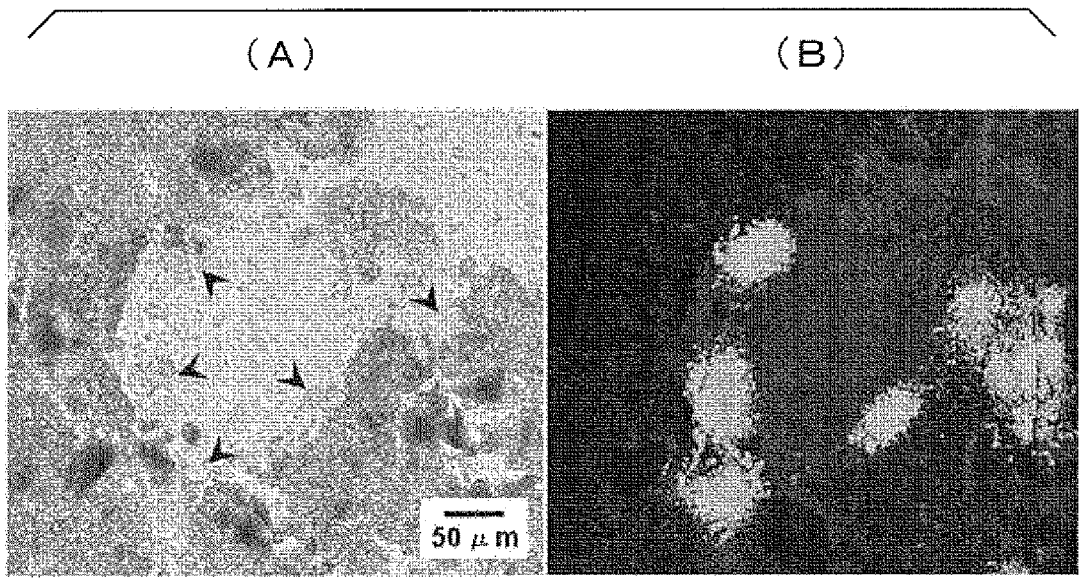
FIG. 25 (A) is an image of a TRAP stained tissue section.

FIG. 25 (A) is an image of a TRAP stained tissue section. FIG. 25 (B) is a Kusabira Orange fluorescence image of the same region. As shown in FIG. 25 (A) and FIG. 25 (B), osteoclast cells were present at the walls of the second pores of the β-tricalcium phosphate porous body. Osteoclast cells had also infiltrated the center of the β-tricalcium phosphate porous body.

Figure 26:
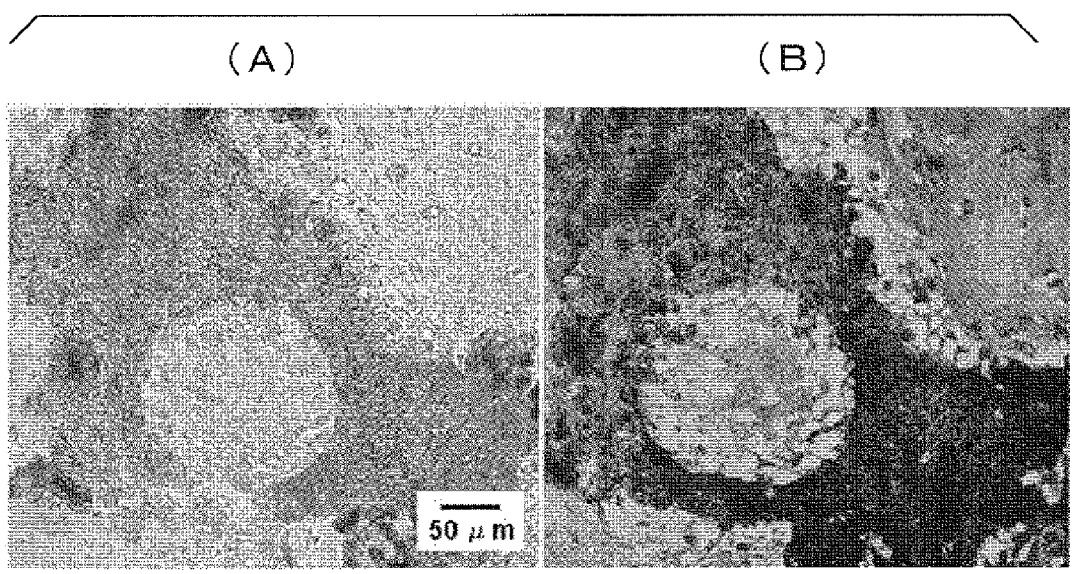
FIG. 26 (A) is an image of an ALP stained tissue section.

FIG. 26 (A) is an image of an ALP stained tissue section. FIG. 26 (B) is a Kusabira Orange fluorescence image of the same region. As shown in FIG. 26 (A) and FIG. 26 (B), osteoblast cells were present along the walls of the second pores of the β-tricalcium phosphate porous body. Osteoblast cells had also infiltrated the center of the β-tricalcium phosphate porous body.

Thus, in the present example, cells had infiltrated the β-tricalcium phosphate porous body implanted in the tibia of the pig clone, and bone growth had occurred along the wall surfaces of the β-tricalcium phosphate porous body.

Example A7

This example illustrates the bioabsorption of a β-tricalcium phosphate porous body implanted in the tibia of the pig clone in the same manner as in example A6 above.

In the present example, images of a cross-section of the β-tricalcium phosphate porous body prior to implantation in the tibia of the pig clone and six months after implantation were captured using a microscope camera (FIG. 27, FIG. 28), and the respective cross-sectional areas were measured and compared.

The present example includes an example of using HAp as the fibrous calcium phosphate material to manufacture a HAp porous body.

Figure 27:
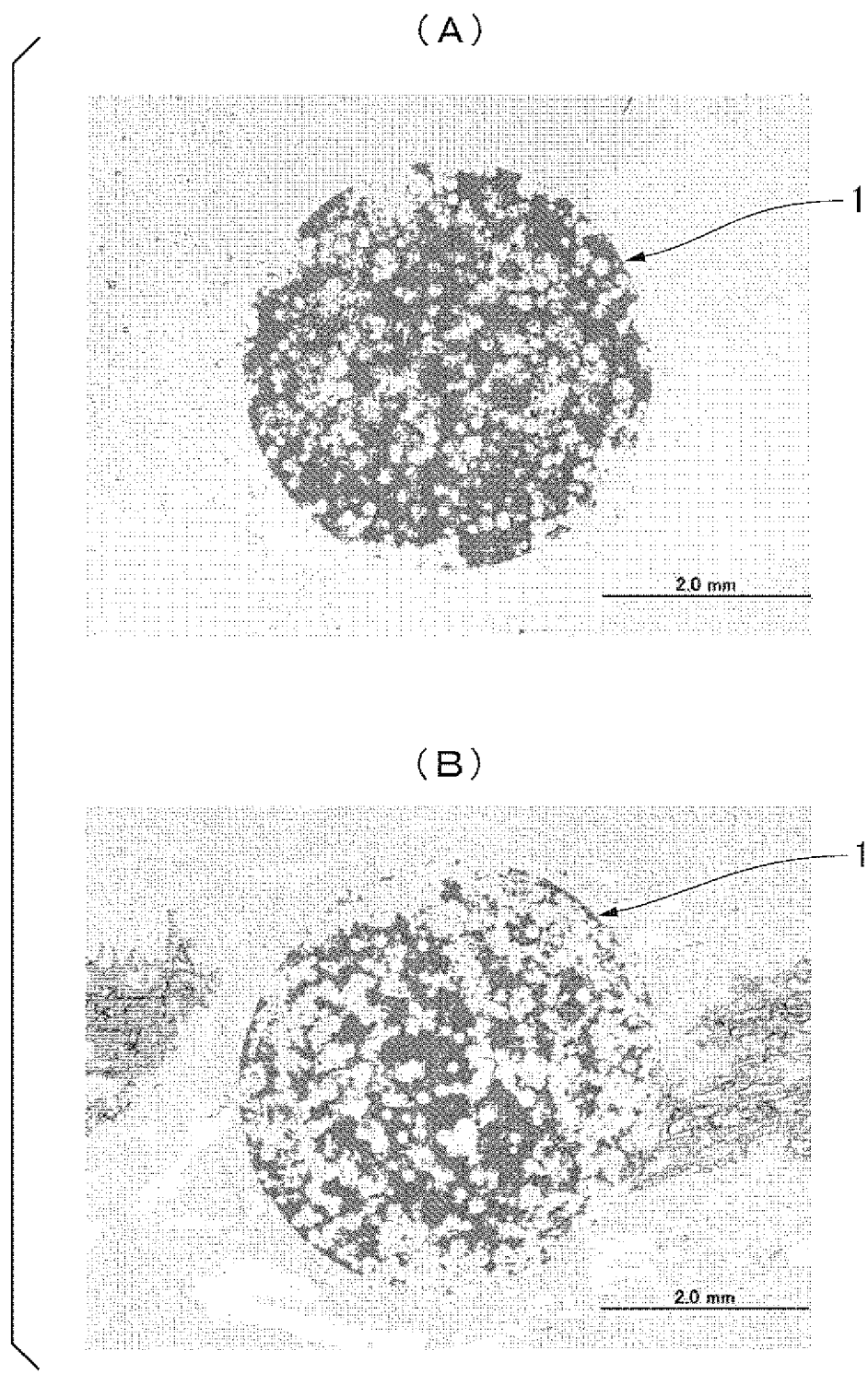
FIG. 27 (A) is an image of a cross-section of β-tricalcium phosphate porous body prior to implantation in a tibia of a cloned pig.

FIG. 27 (A) is an image of a cross-section of the β-tricalcium phosphate porous body prior to implantation in the tibia of the cloned pig. FIG. 27 (B) is an image of a cross-section of the β-tricalcium phosphate porous body six months after implantation.

Figure 28:
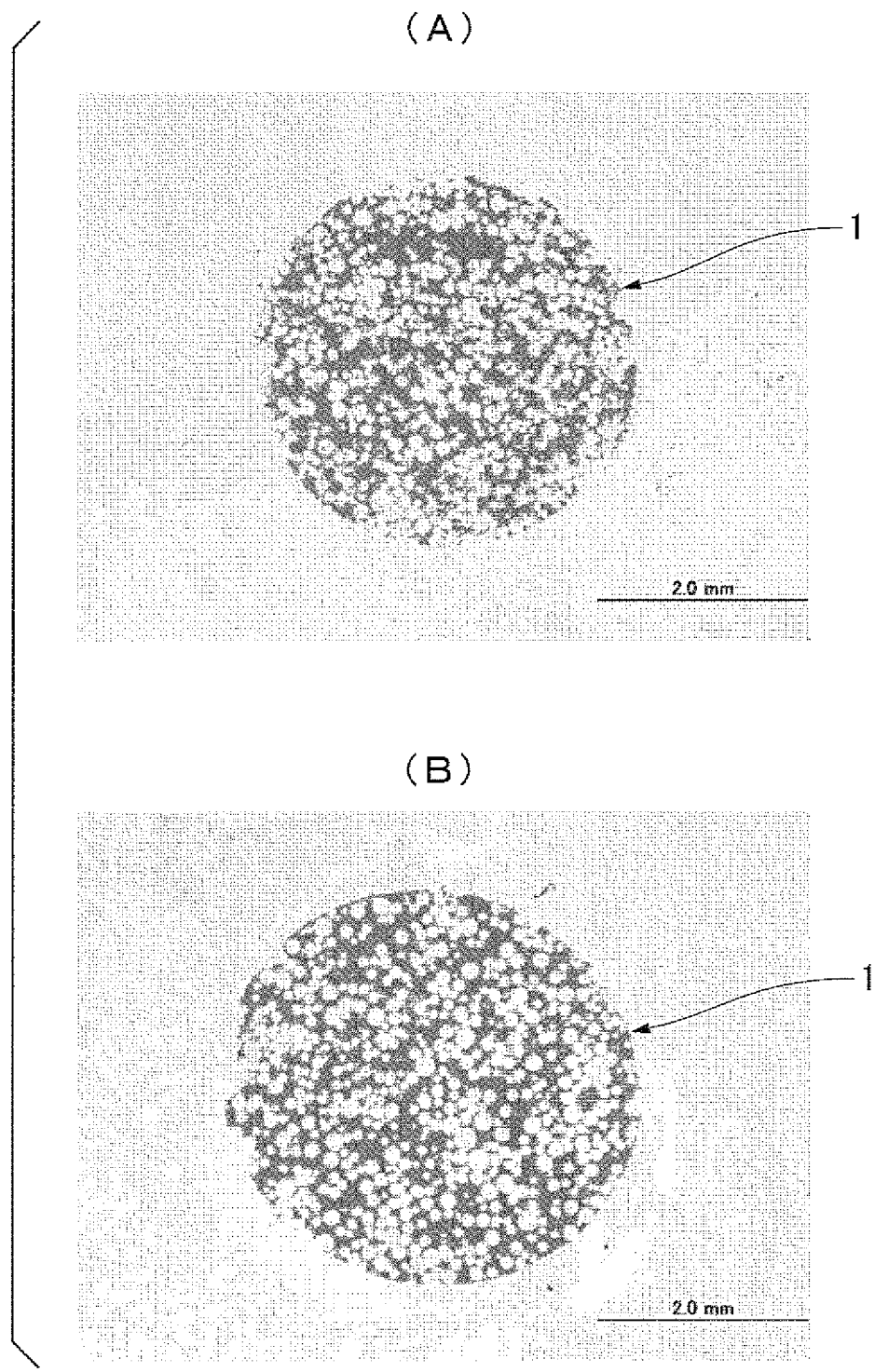
FIG. 28 (A) is an image of a cross-section of a HAp porous body prior to implantation in a tibia of a cloned pig.

FIG. 28 (A) is an image of a cross-section of the HAp porous body prior to implantation in the tibia of the cloned pig. FIG. 28 (B) is an image of a cross-section of the HAp porous body six weeks after implantation.

Figure 29:
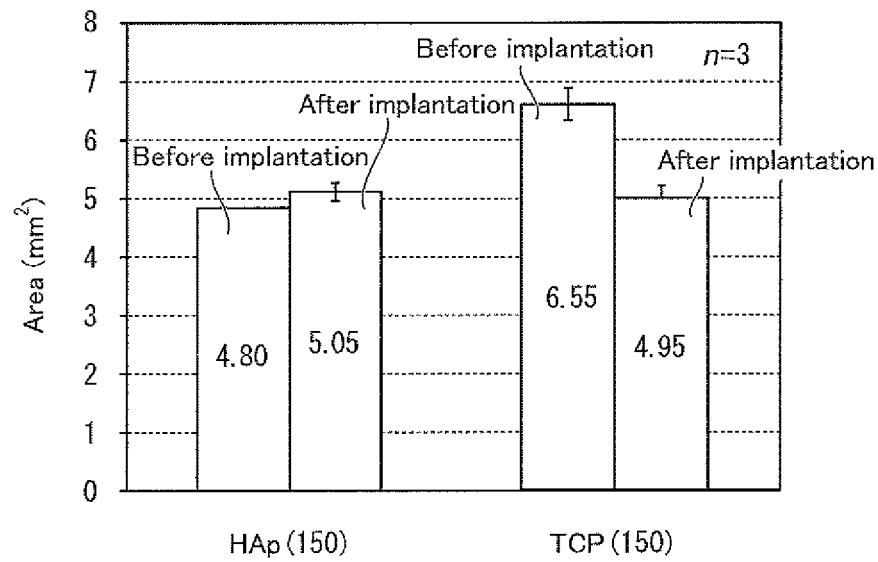
FIG. 29 is a graph showing the results of calculating the area of the calcium phosphate porous body based on the images shown in FIGS. 27 (A) and (B) and FIGS. 28 (A) and (B).

FIG. 29 is a graph showing the results of calculating the area of the calcium phosphate porous body based on the images shown in FIGS. 27 (A) and (B) and FIGS. 28 (A) and (B). In FIG. 29, HAp (150) indicates the results for a HAp porous body manufactured by adding carbon beads with an average particle size of 150 μM, and TCP (150) indicates the results for a β-tricalcium phosphate porous body manufactured by adding carbon beads with an average particle size of 150 μm.

As shown in FIG. 29, the cross-sectional area of the HAp porous body was slightly increased in the sample after implantation, compared with the sample before implantation.

Furthermore, as shown in FIG. 29, the cross-sectional area of the β-tricalcium phosphate porous body had decreased by 25% in the sample after implantation, compared with the sample before implantation. In other words, 25% of the β-tricalcium phosphate porous body was degraded or absorbed during the period of implantation in the cloned pig.

Example A8

This example illustrates the areas of bone growth in β-tricalcium phosphate porous body implanted in the tibia of the cloned pig in the same manner as example A6.

In this example, a microscope camera was used to capture an image of a cross-section of the β-tricalcium phosphate porous body 6 weeks after implantation in the tibia of the cloned pig. Relative to 100% of the total area of the disc-shaped β-tricalcium phosphate porous body before the implantation, the proportion occupied by the β-tricalcium phosphate porous body and the proportion of new bone growth were calculated.

Similarly, the proportion of the HAp porous body and of new bone growth relative to the total area were calculated for the HAp porous body used in example A7.

Figure 30:
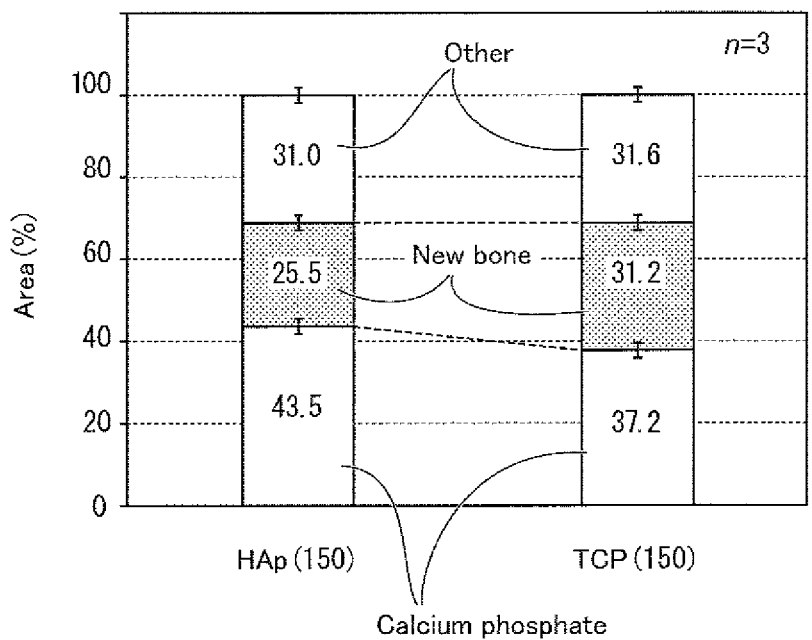
FIG. 30 is a graph showing the area of the bone growth in the β-tricalcium phosphate porous body and the HAp porous body.

FIG. 30 is a graph showing the area of the bone growth in the β-tricalcium phosphate porous body (TCP (150)) and the HAp porous body (HAp (150)). As shown in FIG. 30, the proportion of new bone growth in the β-tricalcium phosphate porous body and the HAp porous body was 31.2% and 25.5% of the total area, respectively. The proportion of new bone growth in the β-tricalcium phosphate porous body was higher than that of the HAp porous body.

Example A9

In this example, samples of a β-tricalcium phosphate porous body (TCP (150)), a β-tricalcium phosphate porous body (TCP (20)) with the average particle size of the carbon beads changed to 20 μm, and a HAp porous body (HAp (150)) using HAp as the fibrous calcium phosphate raw material were created according to the steps described in example A1, and the bone inducing properties of each sample were evaluated in vivo. Table 5 shows the manufacturing conditions of each test piece, and the properties of the materials.

TABLE 5

| Sample | Average particle size of carbon beads | Firing conditions | Pore size (μm) | Porosity (%) |
|---|---|---|---|---|
| TCP (150) | 150 | 1300° C. for 5 hours | 0.2 to 2, and 150 | 72.1 ± 1.8 |
| HAp (150) | 150 | 1000° C. for 5 hours | 0.2 to 2, and 150 | 70.2 ± 1.6 |
| TCP (20) | 20 | 1000° C. for 5 hours | 0.2 to 2, and 150 | 69.6 ± 1.7 |

To evaluate the bone inducing properties of the porous body, the TCP (150), TCP (20), and HAp (150) were molded into cylindrical test pieces with a diameter of 4 mm and height of 8 mm. Each test piece was subjected to dry heat sterilization at 160° C. for 90 minutes before being evaluated.

As the experimental animals, transgenic cloned pigs carrying the red fluorescent protein gene Kusabira Orange (huKO) (huKO pigs, 29 weeks old, male, about 100 kg) were used. After anaesthetizing the huKO pigs using Somnopentyl (Kyoritsu Seiyaku Corporation), the abdomen and the femoral region of the left hind leg were shaved, and a scalpel was used to cut the skin and expose the abdominal adipose tissue and thigh muscle. Pockets approximately 1 cm deep were created in the abdominal adipose tissue and thigh muscle, and after implanting one of each test piece (two in total) in the pockets, the skin was closed using nylon sutures.

13 weeks after the test pieces were implanted in the huKO pig, the huKO pig was sacrificed by an overdose of anesthetic. The implanted test pieces were then removed, and the cell structure was fixed by immersion in a 4% paraformaldehyde phosphate buffer solution (Wako Pure Chemical Industries). The test pieces were then embedded in paraffin and decalcified to give hematoxylin-eosin stained and Masson trichrome stained tissue sections. A histological observation of the tissue sections was performed using a research system microscope (BX5 made by Olympus).

Figure 31:
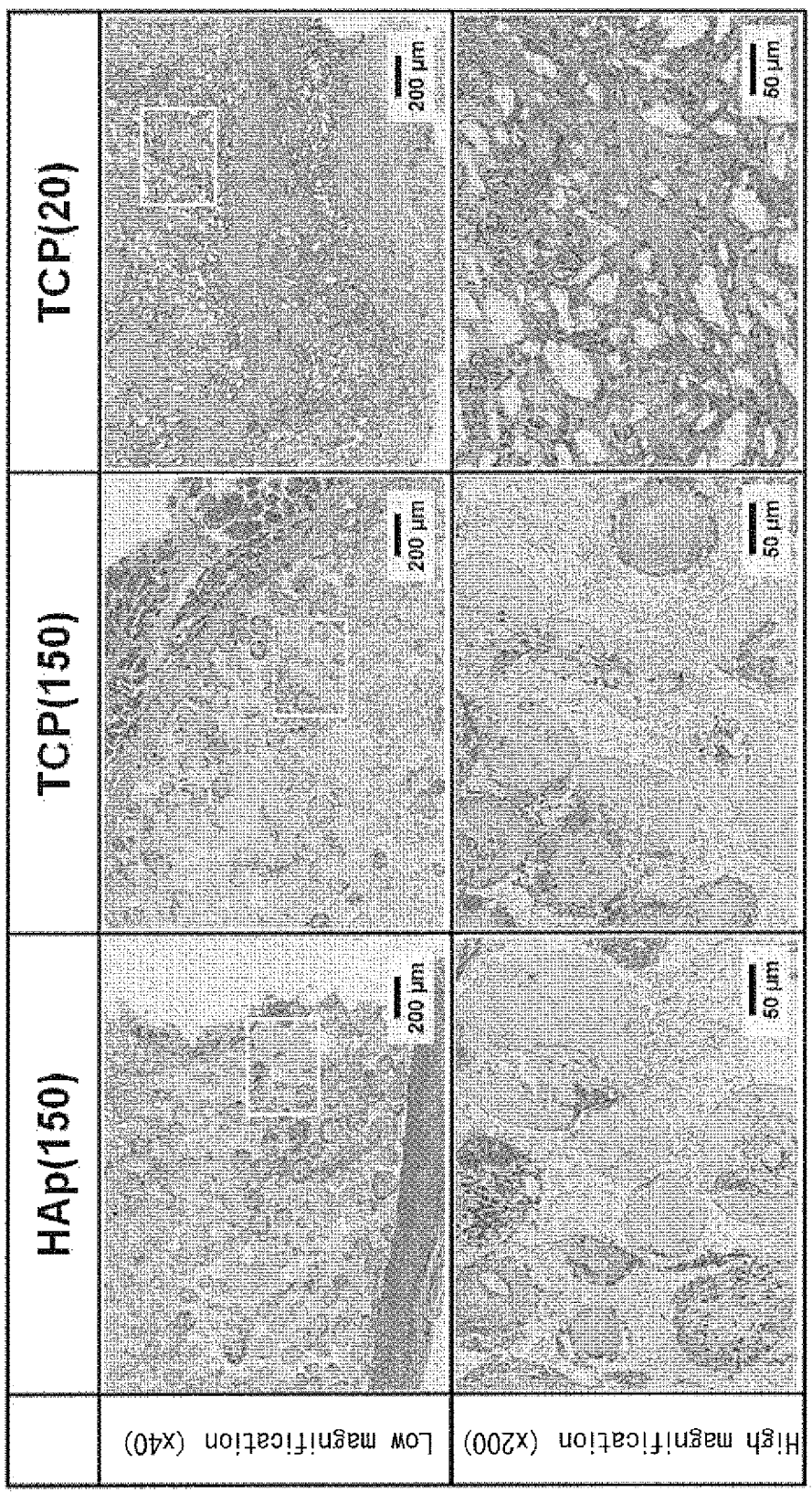
FIG. 31 shows images of Masson trichrome stained sections of the β-tricalcium phosphate porous bodies and HAp porous bodies implanted in muscle tissue.

FIG. 31 shows the results of Masson trichrome staining of the test pieces implanted in the muscle. The top row in FIG. 31 shows an image captured at a low magnification (40×), and the bottom row shows a high power field histological image (200×) of the region demarcated by the square in the top row.

As shown in FIG. 31, bone growth was observed in the round second pores in the samples HAp (150) and TCP (150). On the other hand, no bone growth could be seen in sample TCP (20) after 13 weeks of implantation.

Figure 32:
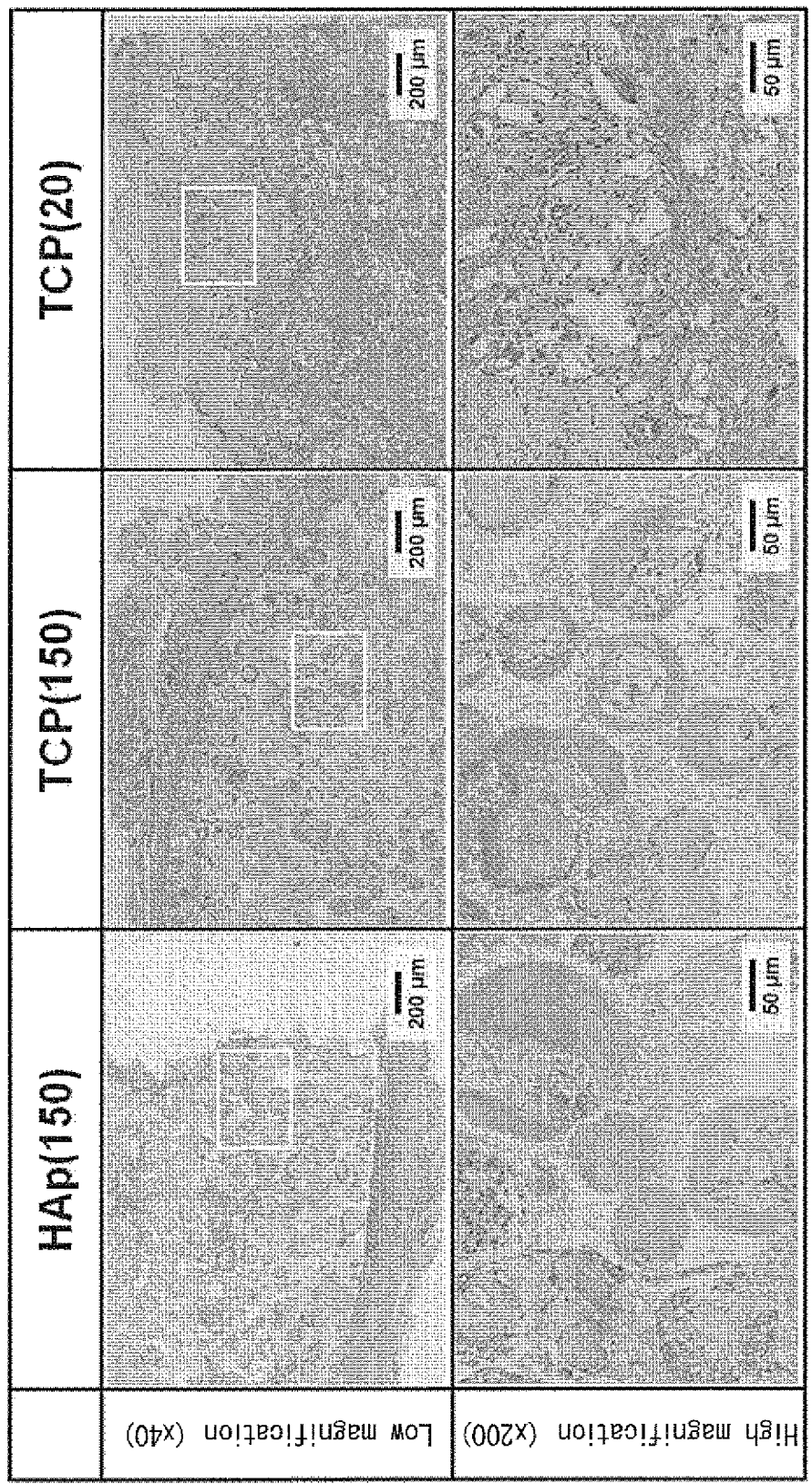
FIG. 32 shows images of hematoxylin and eosin stained sections of the β-tricalcium phosphate porous bodies and HAp porous bodies implanted in muscle tissue.

FIG. 32 shows the results of hematoxylin-eosin staining of the above test pieces. As shown in FIG. 32, bone growth was observed in the round second pores in the porous bodies that used the 150 μm carbon beads (TCP (150) and HAp (150)). The histological findings with respect to samples TCP (150) and HAp (150) indicate that the porous bodies comprising connecting channel structures demonstrate "bone inducing properties" which promote bone growth even in muscle that lacks osteoblasts.

Figure 33:
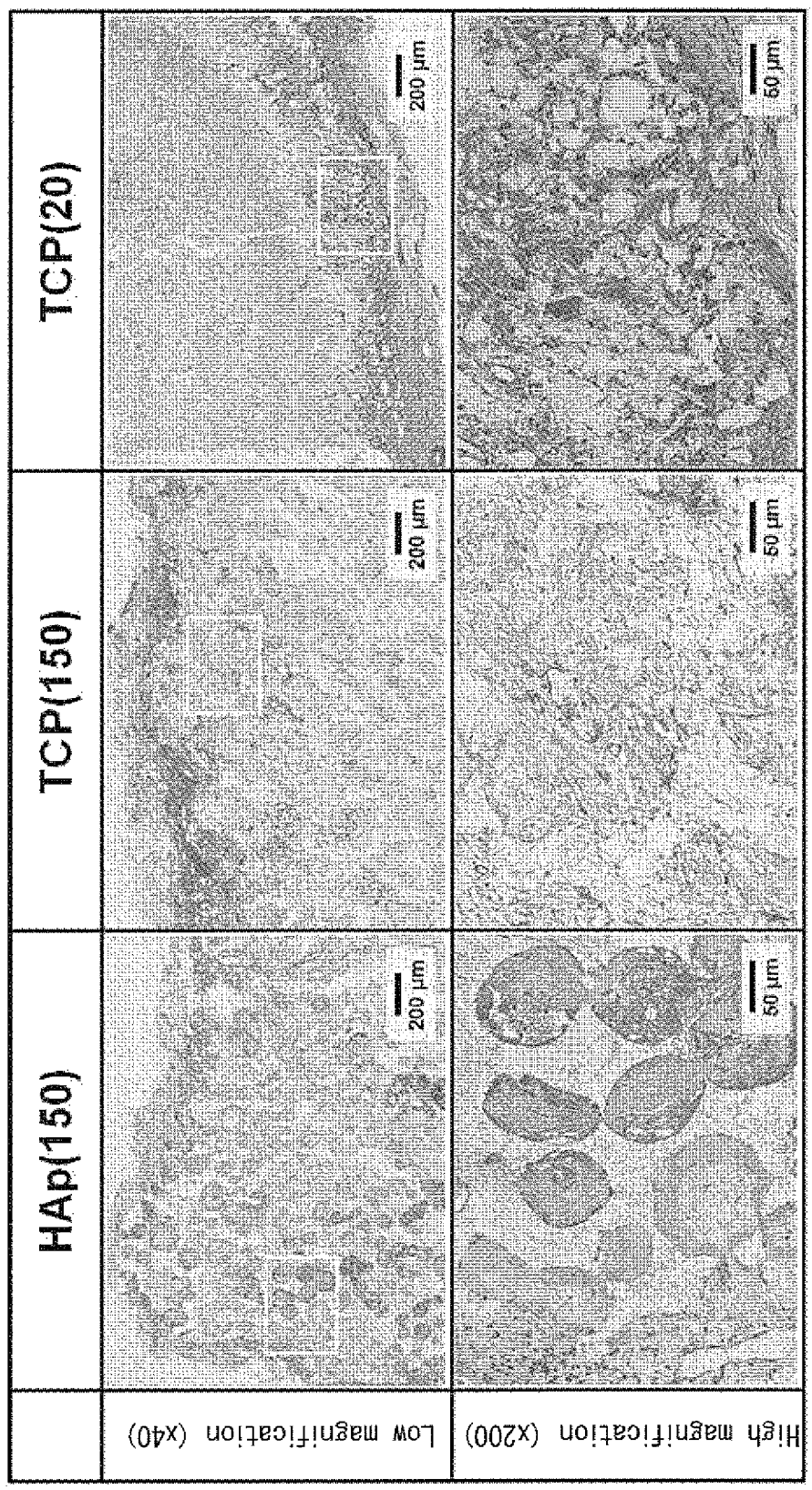
FIG. 33 shows images of Masson trichrome stained sections of the β-tricalcium phosphate porous bodies and HAp porous bodies implanted in adipose tissue.
Figure 34:
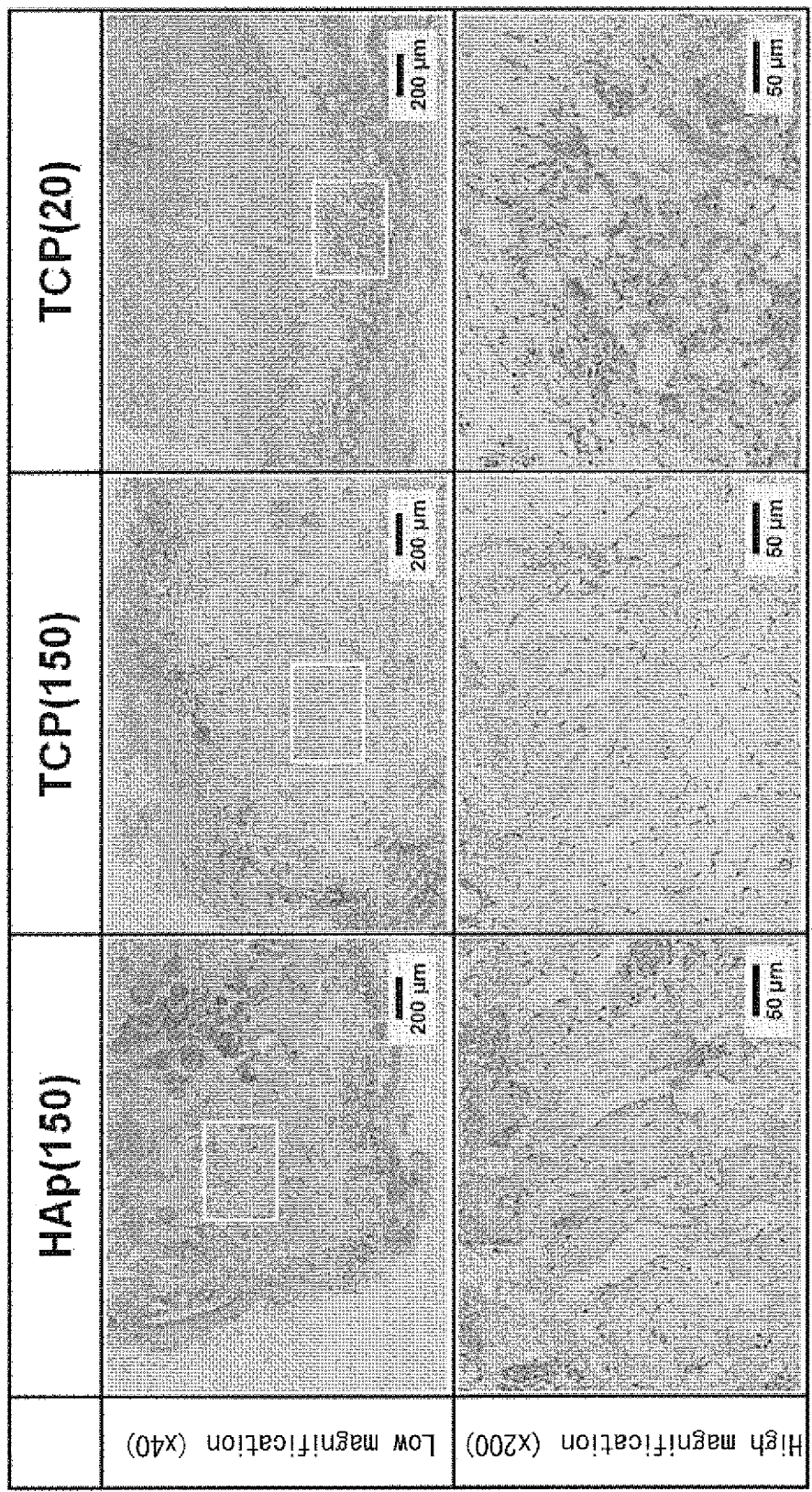
FIG. 34 shows images of hematoxylin-eosin stained sections of the β-tricalcium phosphate porous bodies and HAp porous bodies implanted in adipose tissue.

FIG. 33 and FIG. 34 show the results of implanting the above test pieces in adipose tissue, in the form of histological images of the hematoxylin-eosin stained and Masson trichrome stained tissue sections.

As shown in FIG. 33, in the case of adipose tissue, fibrous tissue had infiltrated the pores and very little bone growth was observed. Furthermore, as shown in FIG. 34, the histological images of the hematoxylin-eosin stained samples, like FIG. 33, showed that fibrous tissue had infiltrated the pores and very little bone growth could be seen.

Example A10

This example illustrates the effects of roughening of the carbon beads.

In the present example, 5 g of carbon beads with an average particle size of 150 μm (Nikabeads®, Nihon Carbon Company) were placed in an alumina boat, and heated under the conditions shown in Table 6 and Table 7 using a Kayo Thermo Systems 1700° C. box electric furnace model KBF31.

TABLE 6

|  | Condition 1 | Condition 2 | Condition 3 |
|---|---|---|---|
| Heating temperature | 1000° C. | 1100° C. | 1200° C. |
| Rate of temperature increase | | 10° C./min | |
| Heating time | | 1 hour | |

TABLE 7

|  | Condition 4 | Condition 5 | Condition 6 | Condition 7 |
|---|---|---|---|---|
| Heating temperature | | 1100° C. | | |
| Rate of temperature increase | | 10° C./min | | |
| Heating time | 0 min | 10 min | 30 min | 60 min |

Figure 35:
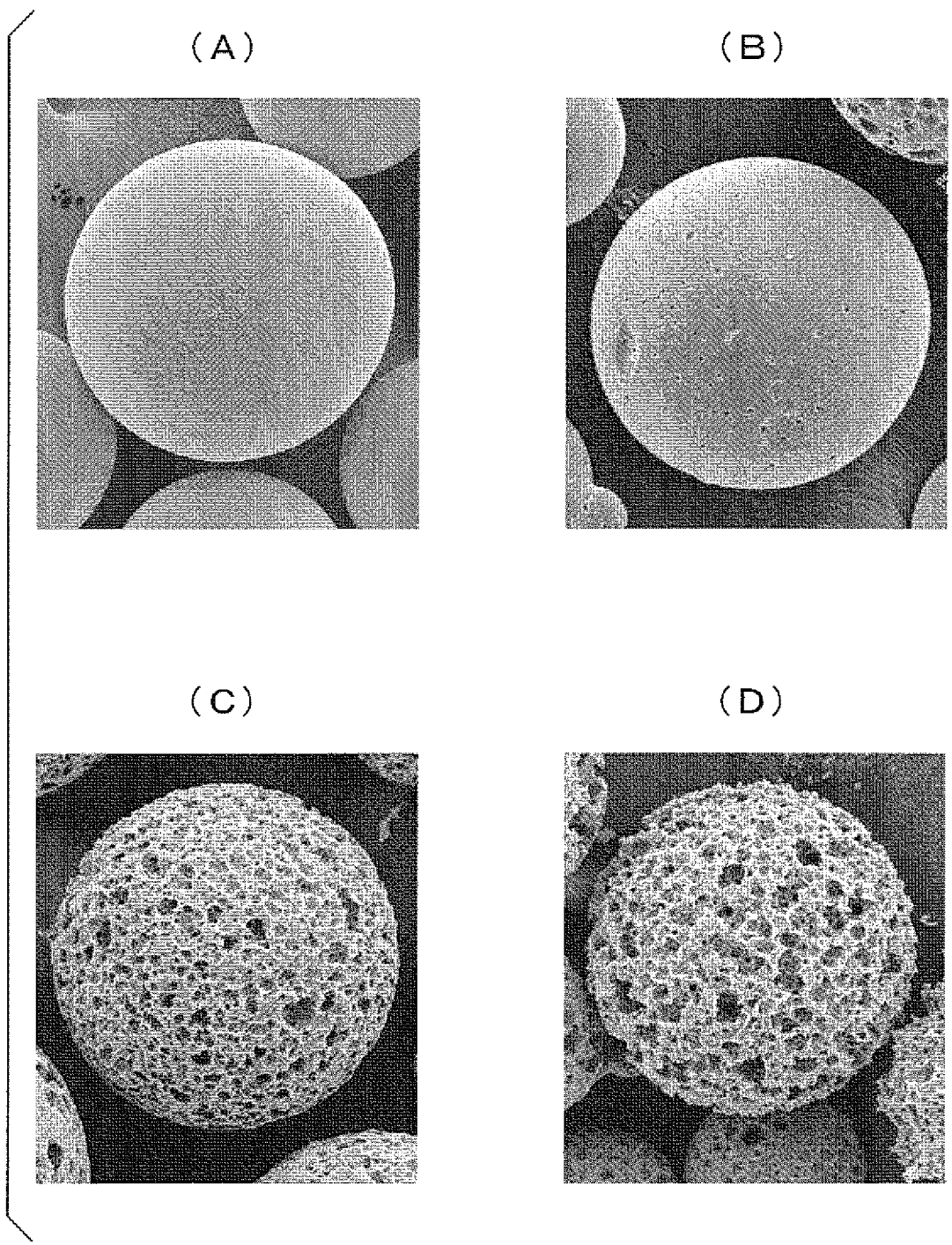
FIG. 35 (A) is an image of unprocessed carbon beads.
Figure 36:
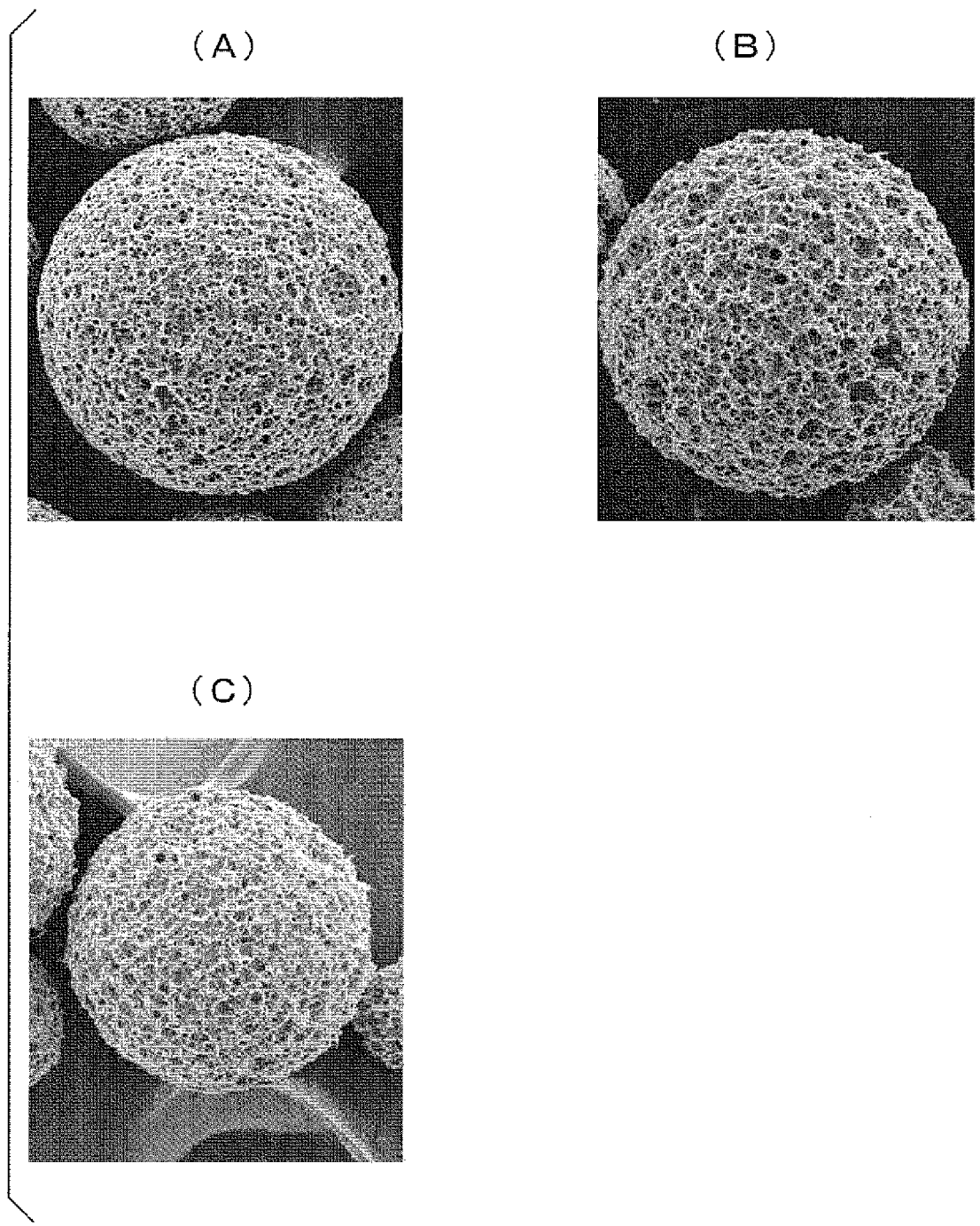
FIGS. 36 (A), (B), and (C) are images of carbon beads subjected to surface roughening by heating for different maintaining time.

FIG. 35 and FIG. 36 both show SEM images, with FIG. 35 (A) showing an image of unprocessed carbon beads. FIG. 35 (B) is an image of carbon beads processed according to condition 1 in Table 6. FIG. 35 (C) is an image of carbon beads processed according to condition 2 in Table 6. FIG. 35 (D) is an image of carbon beads processed according to condition 3 in Table 6.

As shown in FIGS. 35 (A) through (D), the surface roughness of the carbon beads increases as the heating temperature increases. Furthermore, the amount of the loss of the carbon beads increased as the heating temperature increased.

FIG. 36 (A) is an image of carbon beads processed according to condition 4 in Table 7.

FIG. 36 (B) is an image of carbon beads processed according to condition 5 in Table 7. FIG. 36 (C) is an image of carbon beads processed according to condition 6 in Table 7.

Figure 37:
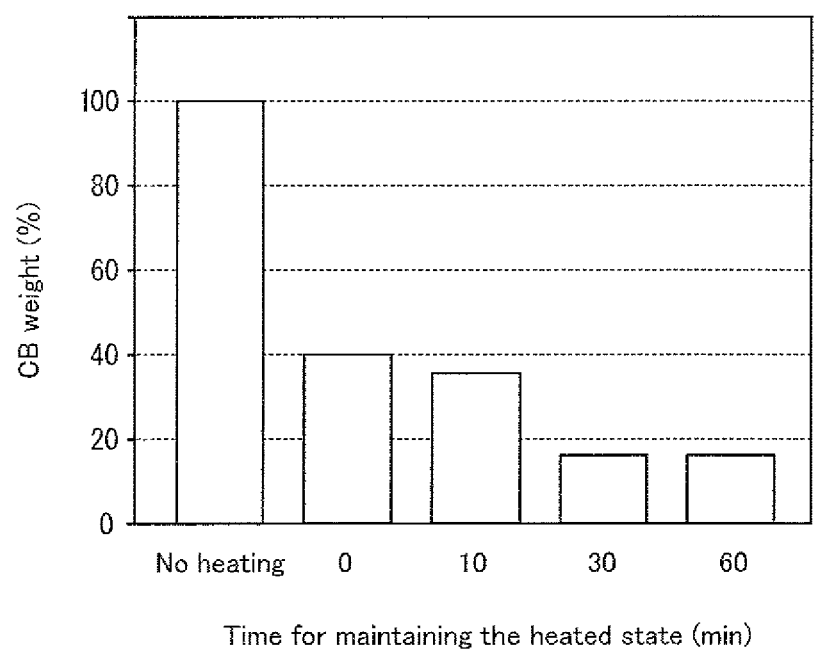
FIG. 37 is a graph showing the mass of the carbon beads subjected to surface processing, with respect to the maintaining time of heating.

FIG. 37 is a graph showing the proportion of the mass of the carbon beads processed according to conditions 4 to 7 in Table 7, relative to the mass of the unheated beads as 100%.

As shown in FIGS. 36 (A) through (C), increasing the length of time where the carbon beads were maintained to be heated had little effect on the surface shape.

Furthermore, as shown in FIG. 37, the mass of the carbon beads decreased until the time for maintaining the carbon beads in the heated state has spent 30 minutes.

In the present example, the time for maintaining the heated state is ideally around 10 minutes.

Example A11

This example describes an example of manufacturing a calcium phosphate porous body using the carbon beads roughened according to condition 5 in example A10 (see FIG. 36 (B)).

In the present example, 5 g of a β-tricalcium phosphate powder (β-TCP-100), 2.5 g of carbon beads roughened according to condition 5, and 0.3 g of Wako Pure Chemical Industries special grade agar were added to 250 cm$^3$ of pure water and heated for 1 hour at 60° C. After adding 107 cm$^3$ of ethanol, the obtained mixture was stirred and left at room temperature to form a gel.

A slurry of the gelled mixture was stirred, poured into a PVC tube with a 16 mm internal diameter, and subjected to suction filtration, after which the filter cake was dried for 24 hours at 60° C. The dried filter cake was gently crumbled to avoid loss of carbon beads, thereby preparing a mixed powder of β-tricalcium phosphate and carbon beads. In addition, 1.0 g of the mixed powder of β-tricalcium phosphate and carbon beads was apportioned and subjected to uniaxial pressing at 100 MPa to prepare a disc-shaped preliminary body (diameter 16 mm, thickness 3 mm).

This disc-shaped preliminary body was then fired under the same conditions as example A1 to give a calcium phosphate porous body.

Figure 38:
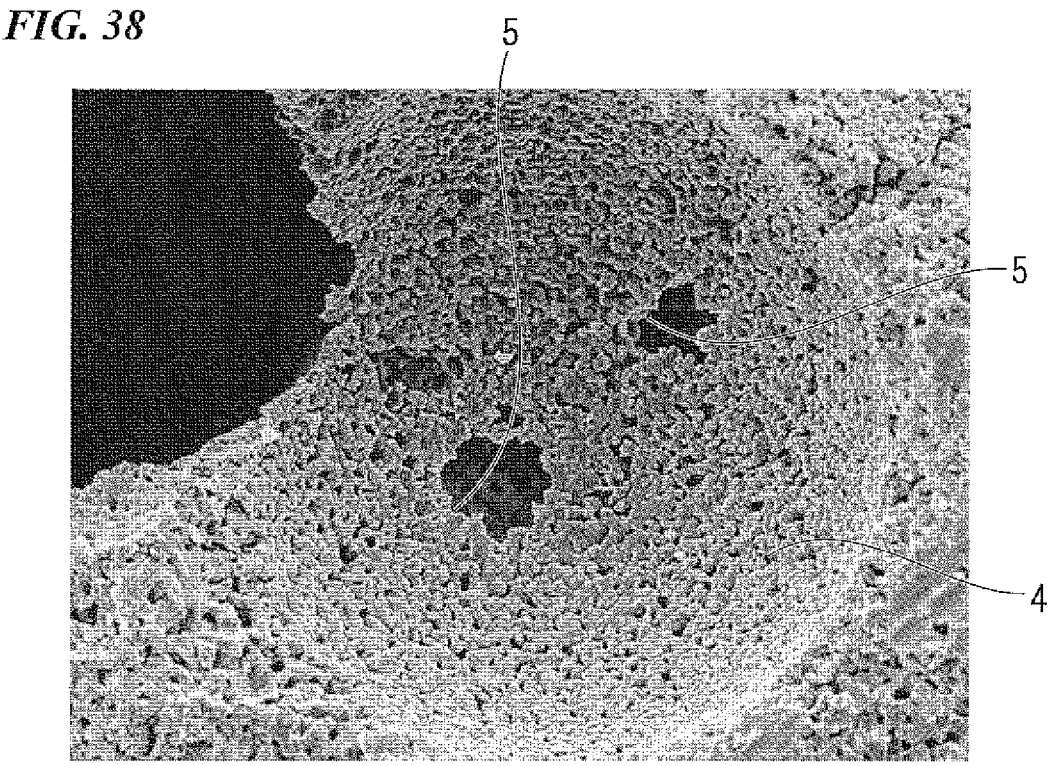
FIG. 38 is an image of a cross-section of a β-tricalcium phosphate porous body manufactured using unroughened carbon beads.
Figure 39:
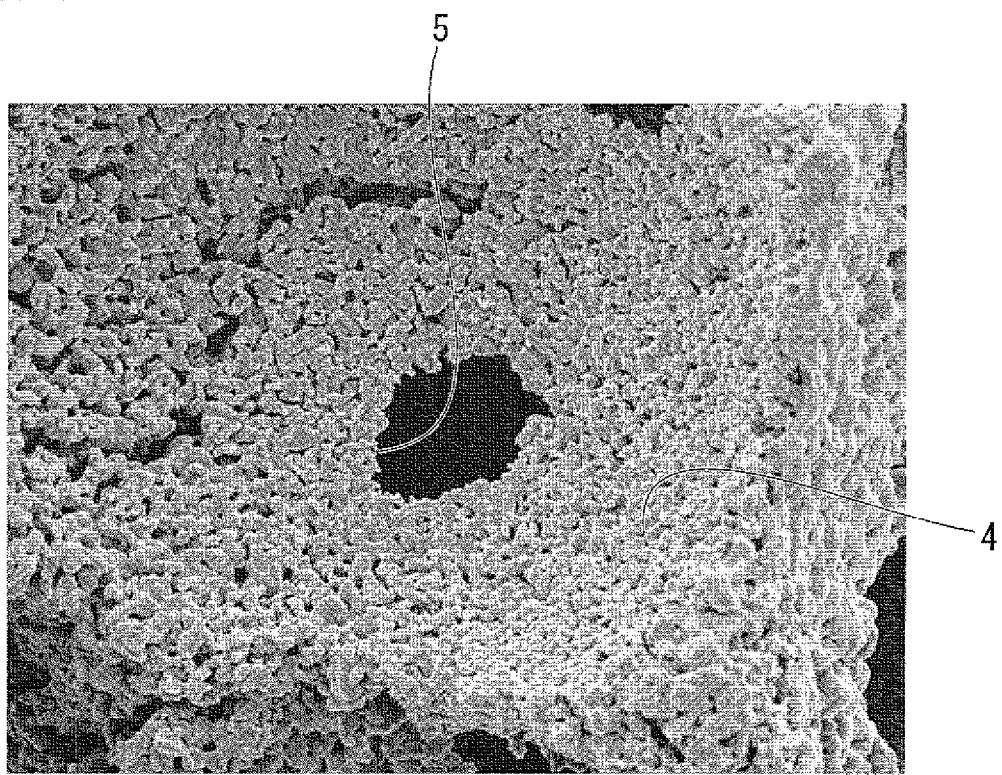
FIG. 39 is an image of a cross-section of a β-tricalcium phosphate porous body manufactured using carbon beads subjected to surface roughening.

As a comparative example, FIG. 38 shows an SEM image illustrating a case where unroughened carbon beads are used. FIG. 39 shows an SEM image of a β-tricalcium phosphate porous body manufactured using carbon beads roughened according to condition 5 in example A10.

As shown in FIG. 38 and FIG. 39, the concavity and convexity of the inside surface of the second pores 4 in the sample produced using the roughened carbon beads was more pronounced than those in the sample that used the unroughened beads, and the diameter of the first connecting channels 5, that connect adjacent second pores 4, in the sample produced using the roughened carbon beads was also larger than that in the sample that used the unroughened beads.

Example A12

This example describes an example of manufacturing a calcium phosphate porous body according to the third embodiment described above.

In the present example, the calcium phosphate porous body was manufactured using carbon beads with an average particle size of 20 μm (first beads) and carbon beads with an average particle size of 150 μm (second beads).

A quantity of carbon beads equivalent to 50% of the fibrous calcium phosphate was added in a 50:50 mixing ratio of first beads and second beads.

All other conditions were the same as example A1.

By this series of steps in the present example, the β-tricalcium phosphate porous body described in the third embodiment was obtained.

Example A13

This example illustrates the relationship between the mixing ratio of the first beads and second beads and the porosity of the β-tricalcium phosphate porous body obtained in example A12.

In this example, in the mixing step, the mixing ratio of the first beads and second beads was 0:10 (first beads only), 5:5, and 10:0 (second beads only).

Figure 40:
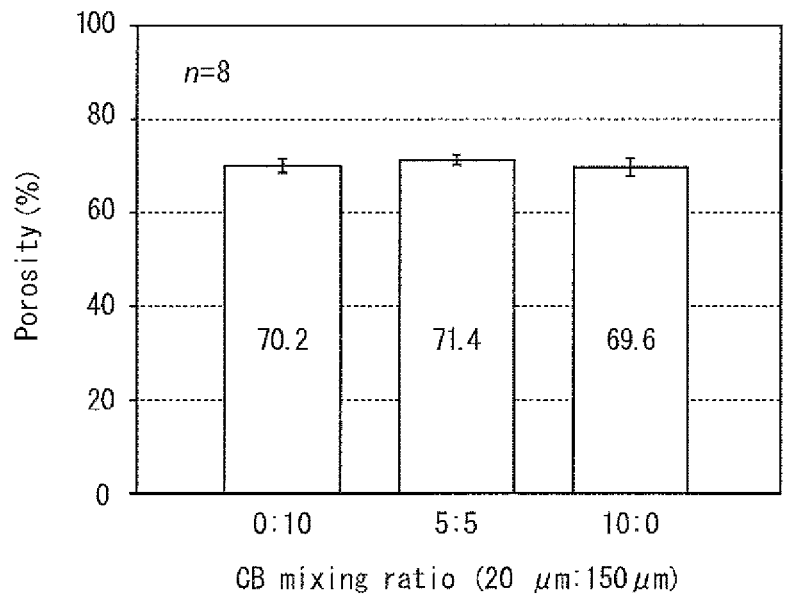
FIG. 40 is a graph showing the relationship of the mixing ratio of the first beads and second beads to the porosity of the β-tricalcium phosphate porous body.

FIG. 40 is a graph showing the relationship of the mixing ratio of the first beads and second beads to the porosity of the β-tricalcium phosphate porous body. As shown in FIG. 40, the porosity was approximately 70% regardless of the mixing ratio of the first beads and second beads.

Example A14

This example illustrates the relationship between the mixing ratio of the first beads and second beads and mechanical strength for the β-tricalcium phosphate porous body obtained in example A13.

In the same manner as example A3 above, mechanical strength was evaluated by measuring the three point bending strength and Young's modulus.

Figure 41:
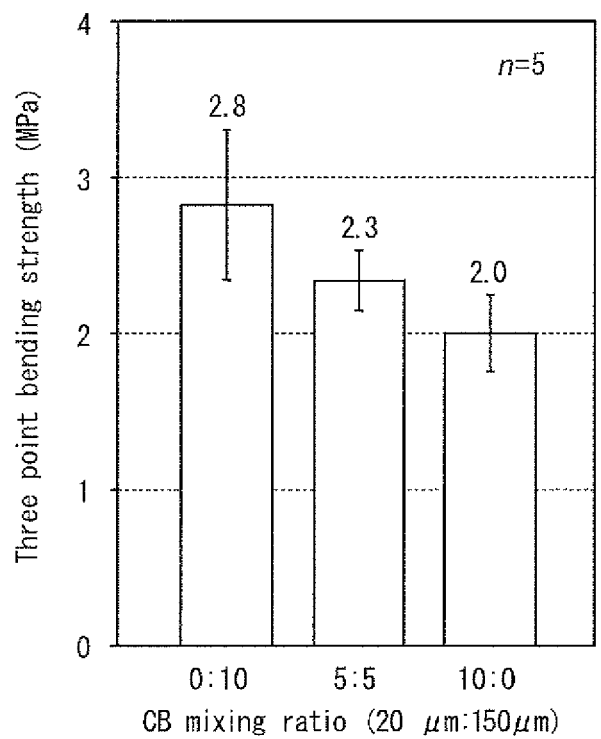
FIG. 41 is a graph showing the three point bending strength calculated for example A15 of the calcium phosphate porous body and manufacturing method according to a third embodiment.
Figure 42:
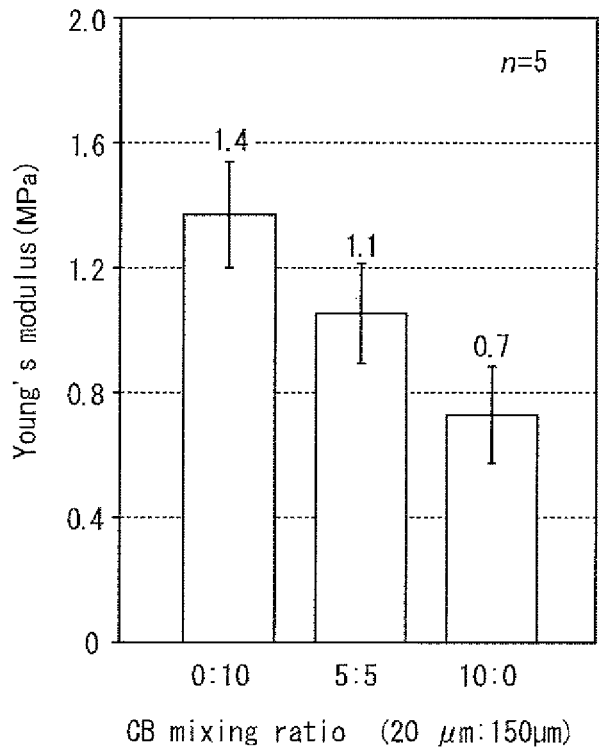
FIG. 42 is a graph showing the Young's modulus for example A15.

FIG. 41 and FIG. 42 are graphs showing the three point bending strength and Young's modulus calculated in this example, respectively. As shown in FIG. 41 and FIG. 42, the three point bending strength and Young's modulus were lower when a greater proportion of the first beads with the small average particle size was added, and higher when a greater proportion of the second beads with the large average particle size was added.

Example A15

This example illustrates the pore size distribution of the β-tricalcium phosphate porous body obtained in example A12.

The pore size distribution of the β-tricalcium phosphate porous body was measured using the same procedure and conditions as in example A5.

Figure 43:
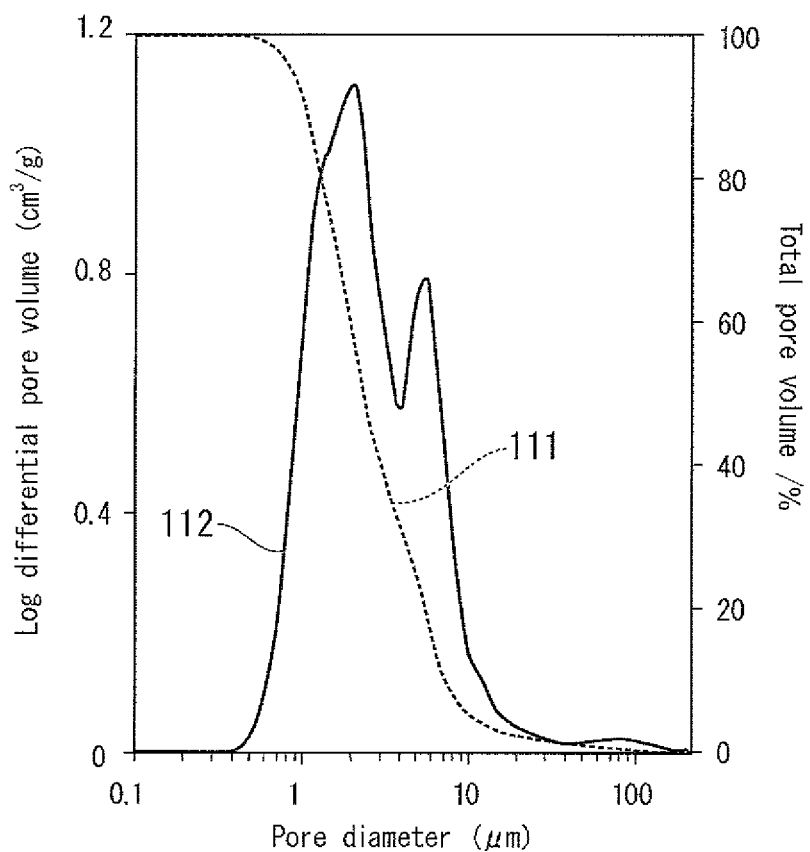
FIG. 43 is a graph showing the relationship between pore diameter and pore volume in the β-tricalcium phosphate porous body in example A15 of the calcium phosphate porous body and manufacturing method according to a third embodiment.

FIG. 43 is a graph showing the relationship between pore diameter and pore volume in the β-tricalcium phosphate porous body of this example. In FIG. 43, the line indicated by reference numeral 111 shows the total pore volume, and the line indicated by reference numeral 112 shows the log differential pore volume.

As shown in FIG. 43, in the present example, the pore size distribution was a curve shape exhibiting two large peaks at 2 μm and 10 μm, and one small peak at 100 μm.

Example A16

This example describes an example of manufacturing a calcium phosphate porous body using only carbon beads with the average particle size of 20 μm, according to the same steps as example A1 above.

Figure 44:
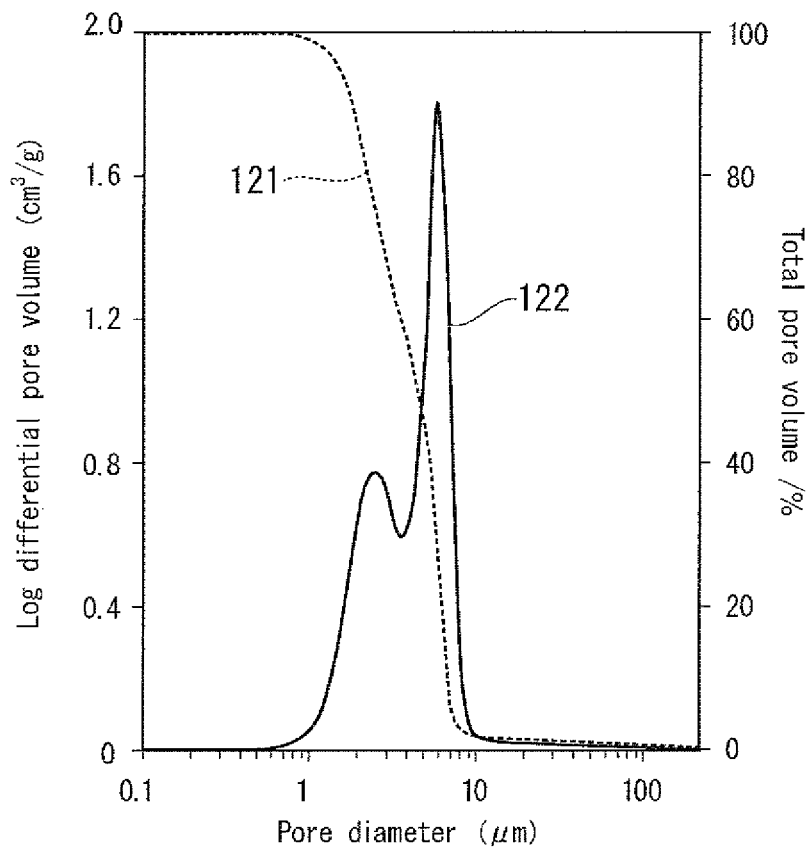
FIG. 44 is a graph showing the relationship between pore diameter and pore volume in the β-tricalcium phosphate porous body in another example of the calcium phosphate porous body and manufacturing method.

FIG. 44 is a graph showing the relationship between pore diameter and pore volume in the β-tricalcium phosphate porous body of this example. In FIG. 44, the line indicated by reference numeral 121 shows the total pore volume, and the line indicated by reference numeral 122 shows the log differential pore volume.

As shown in FIG. 44, in the present example, the pore volume was a curved shape exhibiting two large peaks at 2 μm and 5 μm.

Figure 45:
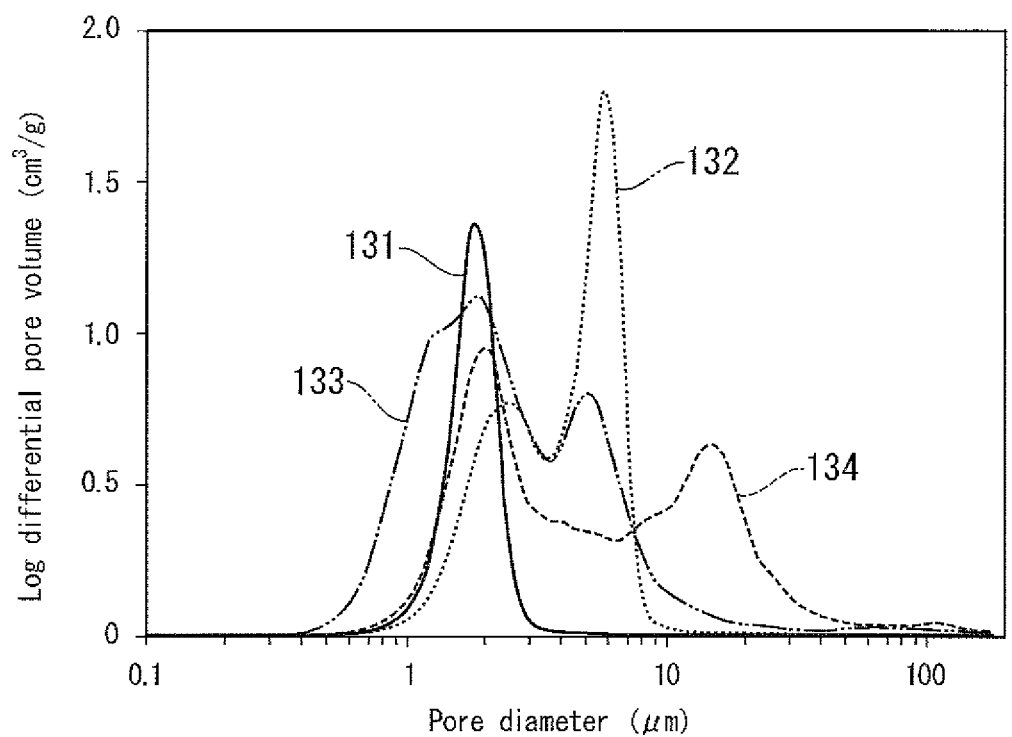
FIG. 45 is a graph that superposes the relationships between pore diameter and log differential pore volume in the β-tricalcium phosphate porous bodies in examples A5, A15, and A16.

FIG. 45 is a graph that superposes the curves indicating the relationships between pore diameter and log differential pore volume in examples A5, A15, and A16, further including the curve indicating the pore size distribution of the calcium phosphate porous body manufactured without carbon beads as a comparative example.

In FIG. 45, the line indicated by reference numeral 131 shows the pore volume of the calcium phosphate porous body that does not contain carbon beads. Furthermore, the line indicated by reference numeral 132 in FIG. 45 shows the pore size distribution of the calcium phosphate porous body to which only the first beads were added. The line indicated by reference numeral 133 in FIG. 45 shows the pore size distribution of the calcium phosphate porous body that contains the first beads and the second beads, and the line indicated by reference numeral 134 in FIG. 45 indicates the pore volume of the calcium phosphate porous body to which only the second beads were added.

As shown in FIG. 45, the calcium phosphate porous body manufactured without adding carbon beads exhibited a single peak in the range from 1 to 3 µm. In contrast, when only the first beads with the average particle size of 20 µm were added, an additional peak was exhibited at about 5 µm.

Furthermore, when only the second beads with the average particle size of 150 µm were added, the calcium phosphate porous body exhibited three peaks at; 1 to 3 µm, about 15 µm, and about 100 µm. In addition, when the first and second beads were both added, two peaks were present at 1 to 3 µm and 7 µm.

Although the present invention has been described in detail with reference to various embodiments and drawings, the detailed construction of the invention is not limited to such embodiments and other embodiments can be devised that do not depart from the scope of the invention.

For example, in the second and third embodiments described above, an example was disclosed in which the fibrous calcium phosphate is composed of β-tricalcium phosphate. However, the fibrous calcium phosphate material is not limited to β-tricalcium phosphate and could be HAp, for example. Moreover, because HAp is a less bioabsorbable material than β-tricalcium phosphate, it can maintain its shape over long periods at bone defect sites.

Furthermore, the fibrous calcium phosphate material can be accordingly chosen for its ability to adjust the speed at which the fibrous calcium phosphate is absorbed into the living body. Furthermore, the fibrous calcium phosphate material could be a mixture of β-tricalcium phosphate and HAp. To increase the speed at which the material is absorbed into the living body, α-tricalcium phosphate can be favorably used instead of β-tricalcium phosphate. In this case, it is preferable to utilize the tendency that α-tricalcium phosphate is produced by firing temperatures exceeding 1150° C.

Furthermore, various combinations of the constituent elements described in the respective embodiments above and the matters described in the examples are possible. For example, the roughening process described in the examples can be applied to any or all of the types of carbon beads with different average particle sizes described in the third embodiment. By this process, the size of the second connecting channels and third connecting channels can be controlled.

Although examples of using carbon beads made primarily of carbon were described in the embodiments and examples above, beads made of a material other than carbon can be selected from known materials.

The present invention can also be used as a porous body and manufacturing method thereof for filling defects in hard tissue like living bone or teeth.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF THE REFERENCE NUMERALS 1, 1A Calcium phosphate porous body
2 Fibrous calcium phosphate
3 First pores
4 Second pores
5 First connecting channels
6 Third pores
7 Second connecting channels
8 Third connecting channels

What is claimed is:

1. A calcium phosphate porous body formed by an intertwining of fibrous calcium phosphates, comprising:
    a plurality of first pores, which are gaps between the fibrous calcium phosphates formed by intertwining the fibrous calcium phosphates with each other;
    a plurality of equal diameter substantially spherical second pores with a larger inside diameter than the first pores;
    a plurality of equal diameter substantially spherical third pores with a larger inside diameter than the first pores and a smaller inside diameter than the second pores, inside diameters of the third pores being 15 to 25 µm; and
    a total porosity is 40 to 70%.

2. The calcium phosphate porous body according to claim 1, comprising first connecting channels which interconnect the second pores.

3. The calcium phosphate porous body according to claim 2, wherein a size of the first connecting channels is within a range from 5 to 30 µm.

4. The calcium phosphate porous body according to claim 1, comprising second connecting channels which connect the second pores and the third pores.

5. The calcium phosphate porous body according to claim 1, comprising third connecting channels which interconnect the third pores.

6. The calcium phosphate porous body according to claim 1, wherein the fibrous calcium phosphate is composed of hydroxyapatite.

7. The calcium phosphate porous body according to claim 1, wherein the fibrous calcium phosphate is composed of β-tricalcium phosphate.

8. A calcium phosphate porous body formed by an intertwining of fibrous calcium phosphates, comprising:
    a plurality of first pores, which are gaps between the fibrous calcium phosphates formed by intertwining the fibrous calcium phosphates with each other;
    a plurality of equal diameter substantially spherical second pores with a larger inside diameter than the first pores;
    first connecting channels which interconnect the second pores, a size of the first connecting channels being within a range from 5 to 30 µm; and
    a total porosity is 40 to 70%.

9. The calcium phosphate porous body according to claim 8, further comprising a plurality of equal diameter substantially spherical third pores with a larger inside diameter than the first pores and a smaller inside diameter than the second pores.

10. The calcium phosphate porous body according to claim 9, comprising second connecting channels which connect the second pores and the third pores.

11. The calcium phosphate porous body according to claim 9, comprising third connecting channels which interconnect the third pores.

12. The calcium phosphate porous body according to claim 8, wherein the fibrous calcium phosphate is composed of hydroxyapatite.

13. The calcium phosphate porous body according to claim 8, wherein the fibrous calcium phosphate is composed of β-tricalcium phosphate.

* * * * *